(12) United States Patent
Takanashi et al.

(10) Patent No.: US 10,031,139 B2
(45) Date of Patent: Jul. 24, 2018

(54) METHOD FOR DETECTING BIOLOGICAL MATERIAL

(71) Applicants: Konica Minolta, Inc., Tokyo (JP); Tohoku University, Sendai-shi, Miyagi (JP)

(72) Inventors: Kensaku Takanashi, Hachioji (JP); Hideki Gouda, Nerima-ku (JP); Keizou Takano, Kokubunji (JP); Hideki Hoshino, Kokubunji (JP); Yasushi Nakano, Hino (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/387,691

(22) PCT Filed: Mar. 28, 2013

(86) PCT No.: PCT/JP2013/059374
§ 371 (c)(1),
(2) Date: Sep. 24, 2014

(87) PCT Pub. No.: WO2013/147081
PCT Pub. Date: Oct. 3, 2013

(65) Prior Publication Data
US 2015/0079611 A1    Mar. 19, 2015

(30) Foreign Application Priority Data

Mar. 30, 2012 (JP) .................................. 2012-080781

(51) Int. Cl.
| | | |
|---|---|---|
| G01N 33/58 | (2006.01) |
| G01N 33/533 | (2006.01) |
| G01N 33/543 | (2006.01) |
| B82Y 30/00 | (2011.01) |
| G01N 1/30 | (2006.01) |

(52) U.S. Cl.
CPC ..... *G01N 33/54393* (2013.01); *G01N 33/533* (2013.01); *G01N 33/582* (2013.01); *G01N 33/585* (2013.01); *B82Y 30/00* (2013.01); *G01N 1/30* (2013.01)

(58) Field of Classification Search
None
See application file for complete search history.

(56) References Cited

U.S. PATENT DOCUMENTS

| | | |
|---|---|---|
| 2005/0112116 A1 | 5/2005 | Lennon |
| 2007/0258895 A1 | 11/2007 | Wang |
| 2009/0115672 A1 | 5/2009 | Yamashita et al. |
| 2009/0116724 A1 | 5/2009 | Yamashita et al. |
| 2010/0141752 A1 | 6/2010 | Yamada et al. |
| 2010/0224831 A1 | 9/2010 | Woo et al. |
| 2013/0157287 A1 | 6/2013 | Takanashi et al. |
| 2014/0212889 A1* | 7/2014 | Gouda ................. G01N 33/569 435/7.1 |
| 2015/0064717 A1* | 3/2015 | Gouda et al. ............ 435/7.5 |

FOREIGN PATENT DOCUMENTS

| | | |
|---|---|---|
| JP | 1-163659 | 6/1989 |
| JP | 2001-525580 | 12/2001 |
| JP | 2005-329141 | 12/2005 |
| JP | 2007-518068 | 7/2007 |
| JP | 2007-528406 | 10/2007 |
| JP | 2008-147394 | 6/2008 |
| JP | 2009-115599 | 5/2009 |
| JP | 2010-134195 | 6/2010 |
| JP | 2010-209314 | 9/2010 |
| WO | 2012/029752 | 3/2012 |

OTHER PUBLICATIONS

Florijin et al., "Analysis of Antifading Reagents for Fluorescence Microscopy," published Aug. 17, 1994.*
Current Protocols in Molecular Biology, "Chapter 14: In Situ Hybridization and Immunohistochemistry," John Wiley & Sons, Inc., published online Oct. 2008.*
Densham et al., "MST Kinases Monitor Actin Cytoskeletal Integrity and Signal via c-Jun N-Terminal Kinase Stress-Activated Kinase to Regulate p21 Waf1/Cip1 Stability", Molecular and Cellular Biology, vol. 29, No. 24, pp. 6380-6390, published Dec. 2009.*
Longin et al., "Comparsion of Anti-fading Agents Used in Fluoresence Microscopy: Image Analysis and Laser Confocal Microscopy Study", Journal of Histochemistry and Cytochemistry, vol. 41, No. 12, pp. 1833-1840, published 1993.*
Jamur et al., "Cell Fixations for Immunostaining", Immunocytochemical Methods and Protocols, vol. 588, pp. 55-61, published Oct. 28, 2009.*
SIGMA, print retrieved internet <https://www.sigmaaldrich.com/content/dam/sigmaaldrich/docs/Sigma/Product_Information_Sheet/1/p3130pis.pdf>, Aug. 31, 2017.*
Japanese Written Opinion of International Searching Authority, International Application No. PCT/JP2013/059374, dated Jun. 15, 2013 (3 pages).

(Continued)

*Primary Examiner* — Tracy Vivlemore
*Assistant Examiner* — Nam P Nguyen
(74) *Attorney, Agent, or Firm* — Lucas & Mercanti, LLP

(57) ABSTRACT

The present invention provides a staining method in which the fluorescent staining properties in a fluorescently-immunostained specimen are not reduced even when an oil-based mounting medium is used. The present invention also provides a method of preventing deterioration of a fluorescent label caused by irradiation with excitation light and improving the light resistance in a fluorescently-immunostained specimen obtained by the staining method. The biological substance detection method according to the present invention is a biological substance detection method for specifically detecting a biological substance from a pathological specimen, which includes the steps of: immunostaining the specimen with a fluorescent label; immobilizing the thus stained specimen; and mounting the thus immobilized specimen using a mounting medium including an organic solvent not freely miscible with water. In the biological substance detection method, the above-described mounting medium further includes a discoloration inhibitor.

9 Claims, No Drawings

(56) References Cited

OTHER PUBLICATIONS

English translatlon of Japanese Written Opinion of International Searching Authority, International Application No. PCT/JP2013/059374, dated Jun. 18, 2013 (5 pages).

European Search Report; dated Nov. 10, 2015; Application No. 13770335.1-1405 / 2833140; Applicant, Konica Minolta, Inc.; Total of 8 pages.

Sweeney E et al: "Quantitative multiplexed quantum dot immunohistochemistry", Biochemical and Biophysical Research Communications, Academic Press Inc. Orlando, FL, US, vol. 374, No. 2, Sep. 19, 2008 (Sep. 19, 2008), pp. 181-186, XP023521452, ISSN: 0006-291X, DOI: 10.1018/J.BBRC.2008.06.127.

G Bock et al: "Photometric Analysis of Antifading Reagents for Immunofluorescence wih Laser and Conventionai Illumination Sources", Journal of Histochemistry and Cytochemistry, Jul. 1, 1985 (Jul. 1, 1985), pp. 699-705, XP055224521, DOI: 10.1177/33.7.2409129.

Zhao Y et al: "Mislocalization of cell-cell adhesion complexes in tamoxifen-resistant breast cancer cells with elevated c-Src tyrosine kinase activity", Cancer Letters, New York, NY, US, vol. 275, No. 2, Mar. 18, 2009 (Mar. 18, 2009), pp. 204-212, XP025915480, ISSN: 0304-3835, DOI; 10.1018/J.CANLET.2008.10.022.

Sweeney E et al., "Quantitative multiplexed quantum dot immunohistochemistry", Biochemical and Biophysical Research Communications, Academic Press Inc. Orland, FL, US, vol. 374, No. 2, Sep. 19, 2008 (Sep. 19, 2008), pp. 181-186XP023521452, ISSN: 006-291X.

G Bock et al, "photometric Analysis of Antifading Reagents for Immunofluorescence with Laser and Conventional Illumination Sources". Journal of Histochemistry and Cytochemistry, Jul. 1, 1985 (Jul. 1, 1985), pp. 599-705, XP055224521, D01: 10.1177/33.7.2409129.

Zhao Y et al, Misloalizationof cell-cell adhesion complexes in tamoxifen-resistant breast cancer cells with elevated c-Src tyronine kinase activity, Cancer Letters, New York, NY, US. vol. 275. No. 2, Mar. 18, 2009 (Mar. 18, 2009), pp. 204-212, XP025915480, ISSN: 0304-3835, D01: 10.1016/J. CANLET. 2008.10.022.

Notification of Reason for Refusal dated Feb. 7, 2017 from corresponding Japanese Patent Application No. JP 2014-508057; English translation of Notification of Reason for Refusal; Total of 3 pages.

Decision of Refusal dated Jul. 18, 2017 from corresponding Japanese Application No. JP 2014-508057 and English translation.

Japanese International Search Report, International Application No. PCT/JP2013/059374, dated Jun. 18, 2013. (2 pages).

English translation of international Search Report, nternational Application No. PCT/JP2013/059374, dated Jun. 18, 2013. (4 pages)

Japanese Written Opinion of International Searching Authority, International Application No. PCT/JP2013/059374, dated Jun. 18, 2013 (3 pages).

English translation of Japanese Written Opinion of International Searching Authority, International Application No. PCT/JP2013/059374, dated Jun. 18, 2013 (5 pages).

* cited by examiner

METHOD FOR DETECTING BIOLOGICAL MATERIAL

CROSS REFERENCE TO RELATED APPLICATION

This Application is a 371 of PCT/JP2013/059374 filed on Mar. 28, 2013 which, in turn, claimed the priority of Japanese Patent Application No. JP2012-080781 filed on Mar. 30, 2012 both applications are incorporated herein by reference.

TECHNICAL FIELD

The present invention relates to a biological substance detection method. More particularly, the present invention relates to tissue staining in which a tissue is stained with a fluorescent label.

BACKGROUND ART

As a medical diagnosis, pathological diagnosis is performed. A pathologist diagnoses a disease using a tissue section collected from human body and informs a clinician of whether or not a therapy and/or surgery is/are necessary. Based on the patient conditions and the pathological diagnosis, a physician determines pharmacotherapeutic strategies and a surgeon determines whether or not a surgery should be performed.

In pathological diagnosis, it is a common practice to prepare a tissue specimen by slicing a tissue sample obtained by evisceration or needle biopsy into a thickness of about several micrometers and then observe the tissue specimen at a magnification under a light microscope so as to obtain various findings. In many cases, a specimen is prepared by fixing a collected tissue through dehydration and paraffin blocking, slicing the thus fixed tissue into a thickness of several micrometers, and then removing the paraffin.

In pathological diagnosis, immunological observation in which molecular target staining called immunostaining is performed for verifying the expression of molecular information of a specimen and functional abnormalities such as abnormal expression of a gene or a protein are diagnosed is performed. For immunostaining, for example, a dye staining method using an enzyme (e.g., DAB staining) is employed. In DAB staining, an antibody modified with peroxidase, which is capable of allowing diaminobenzidine (DAB) to show a color, is used to stain an antigen to be observed with the color and the amount of the antigen is determined by observing the stained antigen. Alternatively, fluorescent labeling may be employed in some cases. In fluorescent labeling, the amount of the subject antigen is determined by staining the antigen with an antibody modified with a fluorescent dye and observing the stained antigen.

Further, since a specimen hardly absorbs or scatters any light and is thus nearly colorless and transparent, it may be subjected to staining with a die for morphological observation prior to being observed. There have been proposed a variety of staining techniques. In particular, for tissue specimens, hematoxylin-eosin staining (HE staining) using two dyes, hematoxylin and eosin, is typically used as staining for observing the morphology of the subject specimen (Non-patent Document 1, Patent Documents 1 and 2). Hematoxylin stains cell nuclei, calcareous parts, cartilaginous tissues, bacteria and mucus in livid to light blue, while eosin stains cytoplasm, interstitial tissues, various fibers, erythrocytes and keratinocyte in red to dark red. A pathologist makes a diagnosis based on the morphological and staining information, such as changes in the size and shape of cell nuclei and changes in the pattern as a tissue, in a micrograph of the stained tissue specimen. Examples of other staining for morphological observation include Papanicolaou staining (Pap staining) used for cytological diagnosis. By subjecting a tissue section to both morphological staining and immunostaining, morphological observation and immunological observation of the specimen can be performed simultaneously.

At present, DAB staining is often used in immunological observation (Patent Document 3). However, in staining with an enzyme label such as DAB staining, since the staining concentration is largely variable depending on the environmental conditions such as temperature and time, there is a problem that estimation of the actual amount of an antibody or the like from the staining concentration is difficult. Therefore, for immunological observation in pathological diagnosis, fluorescent labeling using a fluorescent label is also performed as an alternative to staining with an enzyme label. This method characteristically has superior quantitative capability than DAB staining (Non-patent Document 1).

Observation using a fluorescent label is performed under a confocal laser scanning microscope or epifluorescence microscope. Such microscopes utilize a high-intensity excitation light. For example, as opposed to an intensity of 1,000 W/m$^2$, which is normal sunlight exposure test condition described in the solar cell standard JIS C 8914, the intensity of the irradiation light used by a typical epifluorescence microscope is 100 times stronger.

When the fluorescent label is damaged by excitation light and no longer emits light, a reduction in the signal occurs. Therefore, in the observation using a fluorescent label, the light resistance of the fluorescent label is important.

It is known that fluorescent dyes, inorganic nanoparticles (which may also be referred to as "semiconductor nanoparticle", "quantum dot" or the like) and aggregates thereof are utilized as fluorescent labels (Non-patent Documents 2 and 3, Patent Document 4). It has been reported that, as compared to fluorescent dyes and inorganic nanoparticles, aggregates thereof have an improved light resistance (Patent Document 5). Therefore, from the standpoint of the light resistance, such aggregates are more preferred; however, the aggregates alone do not have sufficient light resistance required for fluorescence microscopy. Here, an aggregate has a higher brightness than that of one dye molecule; therefore, from the standpoint of the signal, an aggregate is more preferred.

In preparation of a specimen, aqueous mounting media and oil-based mounting media are known as mounting media for mounting a stained pathological section. Aqueous mounting media have a problem in that, since their refractive indices are largely different from that of a specimen, it is difficult to make a specimen transparent and to produce a permanent preparation thereof. Meanwhile, oil-based mounting media are characterized in that their refractive indices are not largely different from that of a specimen and can thus make the specimen transparent; and that they are typically used for preparing a permanent preparation that shows good color tone and color development in morphological staining. Accordingly, oil-based mounting media are more preferably used in the preparation of a specimen.

Therefore, also as a mounting medium for an immunostained specimen, a permanent preparation can be produced with an oil-based mounting medium and, when a specimen is subjected to double staining of immunostaining and morphological staining, it is believed that the use of an oil-based mounting medium showing good color tone and color development in morphological staining is more preferred.

However, when a fluorescently-stained specimen is mounted using an oil-based mounting medium, there is a problem that the fluorescent dye elutes into the mounting medium and this impairs the staining properties. Therefore, there is a circumstance that, while an oil-based mounting medium can be used when the specimen is stained without using any fluorescent label, an aqueous mounting medium having the above-described problems must be used when the specimen is stained with a fluorescent label.

In addition, for observation of a fluorescent label, a confocal laser microscope or a fluorescence microscope is used. In fluorescence observation under these microscopes, a stained section is irradiated with a high-intensity excitation light. This excitation light gradually deteriorates a fluorescent label containing a fluorescent dye or the like and this has a great effect in the fluorescence observation and assessment of immunostaining results. Ideally, there is no deterioration of such fluorescent label. Otherwise, it is necessary to improve the light resistance of the fluorescent label.

In order to improve the light resistance of a fluorescent label, it is thought to admix a discoloration inhibitor with a mounting medium. In aqueous mounting media, for example, incases where 4',6-diamidino-2-phenylindole (DAPI) is used as a fluorescent dye, it is attempted to improve the light resistance of DAPI by using a discoloration inhibitor such as 1,4-diazabicyclo[2.2.2]octane (DABCO) or ProLong Gold (registered trademark, manufactured by Molecular Probes Inc.). However, although the use of such discoloration inhibitor alleviates the deterioration of the fluorescent label, since it cannot completely inhibit the deterioration, observation must be made in a short period.

Nevertheless, since the use of an oil-based mounting medium in staining with a fluorescent dye has the above-described problems, oil-based mounting media have not been used in staining with a fluorescent dye. Therefore, there is no motivation to admix a discoloration inhibitor to an oil-based mounting medium and to use the oil-based mounting medium in fluorescent staining, and such an attempt has thus not been made.

PRIOR ART REFERENCES

Patent Documents

[Patent Document 1] Japanese Translated PCT Patent Application Laid-open No. 2001-525580
[Patent Document 2] Japanese Laid-open Patent Application (Kokai) No. 2009-115599
[Patent Document 3] Japanese Laid-open Patent Application (Kokai) No. 2010-134195
[Patent Document 4] Japanese Laid-open Patent Application (Kokai) No. 2010-209314
[Patent Document 5] Japanese Laid-open Patent Application (Kokai) No. 2008-147394

Non-Patent Documents

[Non-patent Document 1] "Shindan ni yakudatsu men-eki soshiki Shindan (Immunohistochemistry Useful for Diagnosis)", Bunkado Co., Ltd., 2007
[Non-patent Document 2] "Synthesis and Applied Technology of Functional Dyes", CMC Publishing Co., Ltd., 2007

[Non-patent Document 3] "Application of Quantum Dot in Life Science", CMC Publishing Co., Ltd., 2007

SUMMARY OF THE INVENTION

Problems to be Solved by the Invention

An object of the present invention is to provide a staining method in which the fluorescent staining properties in a fluorescently-immunostained specimen are not reduced even when an oil-based mounting medium is used. Another object of the present invention is to provide a method of preventing deterioration of a fluorescent label caused by irradiation with excitation light and improving the light resistance in a fluorescently-immunostained specimen obtained by the staining method. Yet another object of the present invention is to provide a kit used for these methods.

Means for Solving the Problems

The present inventors intensively studied to discover that, in staining with a fluorescent label, by immobilizing the subject specimen after binding the fluorescent label thereto, the fluorescent staining properties are not reduced even when an oil-based mounting medium is used to mount the specimen; and that, by incorporating a discoloration inhibitor into the oil-based mounting medium used in this process, the light resistance of the fluorescent label can be largely improved, thereby completing the present invention. In one aspect of the present invention, in order to realize at least one of the above-described objects, the present invention includes the following items.

[1] A biological substance detection method for specifically detecting a biological substance from a pathological specimen, the method comprising the steps of: immunostaining the specimen with a fluorescent label; immobilizing the thus stained specimen; and mounting the thus immobilized specimen using a mounting medium comprising an organic solvent not freely miscible with water.

[2] The biological substance detection method according to [1], wherein the above-described mounting medium comprises a discoloration inhibitor.

[3] A biological substance detection kit used for the biological substance detection method according to [1], the kit comprising: a mounting medium comprising an organic solvent not freely miscible with water; and an instruction manual that describes the above-described biological substance detection method.

[4] A biological substance detection kit used for the biological substance detection method according to [2], the kit comprising: a mounting medium comprising an organic solvent not freely miscible with water and a discoloration inhibitor; and an instruction manual that describes the above-described biological substance detection method.

[5] A pathological specimen used in the biological substance detection method according to [1], wherein the pathological specimen is subjected to: an immunostaining treatment using a fluorescent label for specifically detecting a biological substance; an immobilization treatment; and amounting treatment using a mounting medium comprising an organic solvent not freely miscible with water.

Effects of the Invention

According to the biological substance detection method of [1], a specimen in which the fluorescent staining properties are not impaired in immunostaining with a fluorescent label can be prepared and a permanent preparation can also be prepared. Further, when double staining of immunostaining and morphological staining is performed, a specimen showing good color tone and color development in morphological staining can be prepared.

According to the biological substance detection method of [2], in addition to the above-described effects, a specimen in which the light resistance of a fluorescent label is improved can be prepared as well.

By using the biological substance detection kit according to [3], a specimen prepared by the method of [1] can be obtained.

By using the biological substance detection kit according to [4], a specimen prepared by the method of [2] can be obtained.

The pathological specimen according to [5] is a specimen or permanent preparation obtained by the method of [1] in which the fluorescent staining properties are not impaired, and it is a pathological specimen which, when subjected to double staining of immunostaining with a fluorescent label and morphological staining, shows good color tone and color development in morphological staining.

MODE FOR CARRYING OUT THE INVENTION

The mode for carrying out the invention will now be described; however, the present invention is not restricted thereto.

The biological substance detection method according to a typical embodiment of the present invention is a method of specifically detecting a biological substance from a pathological specimen, which basically comprises: (1) the step of immunostaining a pathological specimen with a fluorescent label; and (2) the step of irradiating the thus stained pathological specimen with excitation light to allow fluorescence to be emitted for detection of a biological substance from the pathological specimen. In the present invention, the step (1) comprises the specimen immobilization step and mounting step.

The step (1) may also comprise other steps such as deparaffinization step and activation step in the same manner as in a general biological substance detection method.

Further, either before or after the step (1), the step of staining a pathological specimen with a staining agent for morphological observation may be incorporated as well. By this, immunostaining with a fluorescent label and morphological staining with a staining agent for morphological observation can be performed simultaneously.

In the present invention, particularly in the step (1) of immunostaining a pathological specimen, (A) a fluorescent dye, (B) a fluorescent nanoparticle, (C) a fluorescent dye-containing nanoparticle or (D) a fluorescent nanoparticle-containing particle can be used as the fluorescent label. From the standpoint of the signal value ratio to noises, which are the fluorescence of eosin and the intrinsic fluorescence of cells, the higher the brightness of the fluorescent label, the more preferred it is. Accordingly, in the present invention, (B) a fluorescent nanoparticle, (C) a fluorescent dye-containing nanoparticle and (D) a fluorescent nanoparticle-containing particle, which have a higher brightness than (A) a fluorescent dye, can be suitably used as the fluorescent label. Further, from the standpoint of attaining higher light resistance, an aggregate of (C) fluorescent dye-containing nanoparticles and an aggregate of (D) fluorescent nanoparticle-containing particles can be particularly suitably used.

The details of the fluorescent label for immunostaining, the immunostaining step, the staining agent for morphological observation and the morphological staining step will now be described below.

[Fluorescent Label for Immunostaining]

In the present invention, the fluorescent label for immunostaining may be any existing fluorescent label as long as it can be used for immunostaining. The fluorescent label for immunostaining may be any of (A) a fluorescent dye, (B) a fluorescent nanoparticle, (C) a fluorescent dye-containing nanoparticle and (D) a fluorescent nanoparticle-containing particle.

[(A) Fluorescent Dye]

The fluorescent dye used in the present invention may be any existing fluorescent dye. It can be obtained or prepared by a known method.

The fluorescent dye to be contained can be selected from, for example, rhodamine-based dye molecules, squarylium-based dye molecules, cyanine-based dye molecules, aromatic ring-based dye molecules, oxazine-based dye molecules, carbopyronine-based dye molecules and pyrromethene-based dye molecules. Alternatively, the fluorescent dye to be contained can also be selected from, for example, Alexa Fluor (registered trademark, manufactured by Invitrogen)-based dye molecules, BODIPY (registered trademark, manufactured by Invitrogen)-based dye molecules, Cy (registered trademark, manufactured by GE Healthcare)-based dye molecules, DY (registered trademark, Dyomics GmbH)-based dye molecules, HiLyte (registered trademark, manufactured by AnaSpec Inc.)-based dye molecules, DyLight (registered trademark, manufactured by Thermo Fisher Scientific K.K.)-based dye molecules, ATTO (registered trademark, manufactured by ATTO-TEC GmbH)-based dye molecules and MFP (registered trademark, manufactured by Mobitec Co., Ltd.)-based dye molecules. The generic names of these dye molecules are designated based on the main structure (skeleton) or registered trademark of the respective compounds; therefore, those of ordinary skill in the art can properly understand the scope of the fluorescent dyes belonging to the respective generic names without having to bear undue trial and error.

Specific examples of the rhodamine-based dye molecules include 5-carboxy-rhodamine, 6-carboxy-rhodamine, 5,6-dicarboxy-rhodamine, rhodamine 6G, tetramethyl rhodamine, X-rhodamine, Texas Red, Spectrum Red and LD700 PERCHLORATE.

Specific examples of the squarylium-based dye molecules include SRfluor 680-carboxylate, 1,3-bis[4-(dimethylamino)-2-hydroxyphenyl]-2,4-dihydroxycyclo butenediylium dihydroxide, bis,1,3-bis[4-(dimethylamino)phenyl]-2,4-dihydroxycyclobutene diylium dihydroxide, bis,2-(4-(diethylamino)-2-hydroxyphenyl)-4-(4-(diethyliminio)-2-hydroxycyclohexa-2,5-dienylidene)-3-oxocyclobut-1-enolate, 2-(4-(dibutylamino)-2-hydroxyphenyl)-4-(4-(dibutyliminio)-2-hydroxycyclohexa-2,5-dienylidene)-3-oxocyclobut-1-enolate, and 2-(8-hydroxy-1,1,7,7-tetramethyl-1,2,3,5,6,7-hexahydropyrido[3,2,1-ij]quinolin-9-yl)-4-(8-hydroxy-1,1,7,7-tetramethyl-2,3,6,7-tetrahydro-1H-pyrido[3,2,1-ij]quinolinium-9(5H)-ylidene)-3-oxocyclobut-1-enolate.

Specific examples of the cyanine-based dye molecules include 1-butyl-2-[5-(1-butyl-1,3-dihydro-3,3-dimethyl-2H-indol-2-ylidene)-penta-1,3-dienyl]-3,3-dimethyl-3H-indolium hexafluorophosphate, 1-butyl-2-[5-(1-butyl-3,3-dimethyl-1,3-dihydro-indol-2-ylidene)-3-chloro-penta-1,3-dienyl]-3,3-dimethyl-3H-indolium hexafluorophosphate, and 3-ethyl-2-[5-(3-ethyl-3H-benzothiazol-2-ylidene)-penta-1,3-dienyl]-benzothiazol-3-ium iodide.

Specific examples of the aromatic ring-based dye molecules include N,N-bis-(2,6-diisopropylphenyl)-1,6,7,12-(4-tert-butylphenoxy)-perylene-3,4,9,10-tetracarbonacid diimide, N,N'-bis(2,6-diisopropylphenyl)-1,6,7,12-tetraphenoxyperylene-3, 4:9,10-tetracarboxdiimide, N,N'-bis(2,6-diisopropylphenyl)perylene-3,4,9,10-bis (dicarbimide), 16,N,N'-bis(2,6-dimethylphenyl)perylene-3, 4,9,10-tetracarboxylic diimide, 4,4'-[(8,16-dihydro-8,16-dioxodibenzo[a,j]perylene-2,10-diyl)dioxy]dibutyric acid, 2,10-dihydroxy-dibenzo[a,j]perylene-8,16-dione, 2,10-bis (3-aminopropoxy)dibenzo[a,j]perylene-8,16-dione, 3,3'-[(8, 16-dihydro-8,16-dioxodibenzo[a,j]perylene-2,10-diyl)dioxy]dipropylamine, 17-bis(octyloxy)anthra[9,1,2-cde-]benzo[rst]pentaphene-5-10-dione, octadecanoic acid, 5,10-dihydro-5,10-dioxoanthra[9,1,2-cde]benzo[rst]pentaphene-16,17-diylester, dihydroxydibenzanthrone, benzenesulfonic acid, 4,4',4'',4'''-[[2,9-bis[2,6-bis(1-methylethyl)phenyl]-1, 2,3,8,9,10-hexahydro-1,3,8,10-tetraoxoanthra[2,1,9-def:6,5, 10-d'e'f']diisoquinoline-5,6,12,13-tetrayl]tetrakis(oxy)]tetrakis, benzeneethanaminium, and 4,4',4'',4'''-[[2,9-bis[2,6-bis(1-methylethyl)phenyl]-1,2,3,8,9,10-hexahydro-1,3,8, 10-tetraoxoanthra[2,1,9-def:6,5,10-d'e'f']diisoquinoline-5,6, 12,13-tetrayl]tetrakis(oxy)]tetrakis[N, N,N-trimethyl-].

Specific examples of the oxazine-based dye molecules include Cresyl violet, Oxazine 170, EVOblue 30 and Nile Blue.

Specific examples of the carbopyronine-based dye molecules include CARBOPYRONIN 149.

Specific examples of the pyrromethene-based dye molecules include PYRROMETHENE 650.

Specific examples of the Alexa Fluor-based dye molecules include Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 (all of which are manufactured by Invitrogen).

Specific examples of the BODIPY-based dye molecules include BODIPY FL, BODIPY TMR, BODIPY 493/503, BODIPY 530/550, BODIPY 558/568, BODIPY 564/570, BODIPY 576/589, BODIPY 581/591, BODIPY 630/650 and BODIPY 650/665 (all of which are manufactured by Invitrogen).

Specific examples of the Cy-based dye molecules include Cy 3.5, Cy 5 and Cy 5.5 (all of which are manufactured by GE Healthcare).

Specific examples of the DY-based dye molecules include DY-590, DY-610, DY-615, DY-630, DY-631, DY-632, DY-633 and DY-634 (all of which are manufactured by Dyomics GmbH).

Specific examples of the HiLyte-based dye molecules include HiLyte 594 and HiLyteFluor TR (both of which are manufactured by AnaSpec Inc).

Specific examples of the DyLight-based dye molecules include DyLight 594 and DyLight 633 (both of which are manufactured by manufactured by Thermo Scientific).

Specific examples of the ATTO-based dye molecules include ATTO 590, ATTO 610, ATTO 620, ATTO 633 and ATTO 655 (all of which are manufactured by ATTO-TEC GmbH).

Specific examples of the MFP-based dye molecules include MFP 590 and MFP 631 (both of which are manufactured by Mobitec Co., Ltd.).

Examples of other dyes include C-phycocyanin, phycocyanin, APC (allophycocyanin), APC-XL and NorthernLights 637 (all of which are manufactured by R&D Systems, Inc.).

Further, examples of other dyes also include derivatives of the above-described dyes (which can function as a fluorescent dye, such as known derivatives).

[(B) Fluorescent Nanoparticle]

The fluorescent nanoparticle used in the present invention has a particle size of 1 to 500 nm, preferably 10 to 200 nm.

The fluorescent nanoparticle is composed of a semiconductor or fluorophore.

As the semiconductor, for example, a group II-VI semiconductor such as ZnSe, ZnTe, CdSe, CdTe, PbS, PbSe or PbTe, or a group II-VI semiconductor such as AlAs, AlSb, GaP, GaAs, GaSb, InP, InAs or InSb can be used. From the standpoint of toxicity, GaP or InP can be suitably used.

In the fluorophore, for example, $Y_2O_3$, $YVO_4$, ZnO or ZnS can be used as the matrix and Eu or Nd can be used as the emission center.

An excitation wavelength suitable for observation is attained by adjusting the particle size, matrix composition and impurity amount of the fluorescent nanoparticle.

[(C) Fluorescent Dye-Containing Nanoparticle]

From the standpoint of the signal value ratio to noises, which are the fluorescence of eosin and the intrinsic fluorescence of cells, the higher the brightness of the fluorescent label, the more preferred it is. Accordingly, in the present invention, a fluorescent dye-containing nanoparticle having a higher brightness than a fluorescent dye is suitably used as the fluorescent label.

The term "fluorescent dye-containing nanoparticle" refers to a nano-sized particle having a structure in which plural fluorescent dyes are contained in a particle (matrix) made of an organic or inorganic material. The fluorescent dye-containing nanoparticle used in the present invention can be prepared by a known method upon selecting, as raw materials, appropriate fluorescent dyes and particle-forming organic or inorganic material.

Examples of the particle-forming organic or inorganic material include those which are capable of stably containing fluorescent dyes, such as polystyrene, polyamide, polylactic acid, polyacrylonitrile, polyglycidyl methacrylate, polymelamine, polyurea, polybenzoguanamine, polyfuran, polyxylene, phenol resins, polysaccharides and silica. When fluorescent dyes are incorporated into such a particle, deterioration caused by irradiation with excitation light is less likely to occur (higher light resistance is attained) as compared to a case where the fluorescent dyes are used by themselves.

As the fluorescent dyes to be contained, those fluorescent dyes that are exemplified above for the (A) fluorescent dye can be used. In addition, for example, derivatives thereof (which can function as a fluorescent dye, such as known derivatives) can also be used.

In the fluorescent dye-containing nanoparticle, any one of the above-described fluorescent dyes may be contained individually, or a plurality thereof may be contained in combination.

For example, fluorescent dyes such as aromatic ring-based dye molecules and rhodamine-based dye molecules are preferred because of their relatively high light resistance. Thereamong, perylenes belonging to the aromatic ring-based dye molecules, particularly perylene diimide, is preferred. Meanwhile, even when a fluorescent dye having a relatively low light resistance is used, by selecting an appropriate matrix, it is possible to produce a fluorescent dye-containing nanoparticle which satisfies the prescribed condition of brightness retention rate according to the present invention.

The method of producing the fluorescent dye-containing nanoparticle is not particularly restricted. For introduction of a dye(s) into a particle, any method such as a method of synthesizing a particle by binding a dye molecule (s) to a monomer used as raw material of the particle or a method of introducing a dye(s) to a particle by adsorption may be employed.

The average particle size of the fluorescent dye-containing nanoparticle is not particularly restricted; however, it is usually 10 to 500 nm, preferably 50 to 200 nm. Further, the variation coefficient which indicates the variation in the particle size is also not particularly restricted; however, it is usually 20% or less, preferably 5 to 15%. Here, the particle size of a fluorescent dye-containing nanoparticle can be determined by taking an electron micrograph thereof using a scanning electron microscope (SEM), measuring the cross-sectional area of the fluorescent dye-containing nanoparticle and then determining the particle size as the diameter of a circular area corresponding to the measured value (area equivalent circle diameter). With regard to the average particle size (average particle diameter) and the variation coefficient of a group of fluorescent dye-containing nanoparticles, after measuring the particle sizes (particle diameters) for a sufficient number (for example, 1,000) of fluorescent dye-containing nanoparticles in the above-described manner, the average particle size is calculated as the arithmetic mean of the measured values and the variation coefficient is calculated by the following equation: 100×(standard deviation of particle size)/(average particle size).

[(D) Fluorescent Nanoparticle-Containing Particle]

The fluorescent nanoparticle-containing particle used in the present invention is a particle made of an organic or inorganic material that contains the fluorescent nanoparticles explained in the above (B). In the fluorescent nanoparticle-containing particle, any one of the above-described fluorescent nanoparticles may be contained individually, or a plurality thereof may be contained in combination.

The method of producing the fluorescent nanoparticle-containing particle is not particularly restricted. For introduction of a fluorescent nanoparticle(s) into a particle, any method such as a method of synthesizing a particle by binding a fluorescent nanoparticle(s) to a monomer used as raw material of the particle or a method of introducing a fluorescent nanoparticle(s) to a particle by adsorption may be employed. An excitation wavelength suitable for observation is attained by adjusting the particle size, matrix composition and impurity amount of the fluorescent nanoparticle(s) to be contained.

The fluorescent nanoparticle-containing particle has a size of usually 10 to 500 nm, preferably 50 to 200 nm.

[Step of Staining for Morphological Observation]

In the present invention, staining can be performed for morphological observation. In the step of staining for morphological observation, particularly when the morphology of a tissue specimen is observed, the above-described hematoxylin-eosin staining (HE staining) which utilizes two dyes (hematoxylin and eosin) is typically employed; however, in the present invention, the staining for morphological observation is not restricted thereto. Examples of other staining for morphological observation include Papanicolaou staining (Pap staining) used for cytological diagnosis.

In HE staining, hematoxylin stains cell nuclei, calcareous parts, cartilaginous tissues, bacteria and mucus in livid to light blue, while eosin stains cytoplasm, interstitial tissues, various fibers, erythrocytes and keratinocyte in red to dark red. In other staining for morphological observation, a hematoxylin analogue or a dye having an absorption wavelength similar to that of hematoxylin may stain cell nuclei, calcareous parts, cartilaginous tissues, bacteria and mucus in livid to light blue, and an eosin analogue or a dye having absorption and emission wavelengths similar to those of eosin may stain cytoplasm, interstitial tissues, various fibers, erythrocytes and keratinocyte in red to dark red.

[Immunostaining Step]

In the present invention, as an immunostaining method, a fluorescent staining method in which a biological substance to be detected is stained with the above-described fluorescent label for immunostaining is employed.

For example, when immunostaining a specific antigen, a method in which a label (conjugate) is prepared by directly binding a fluorescent label and a primary antibody and an antigen is then stained (primary antibody method), a method in which a label is prepared by directly binding a fluorescent label and a secondary antibody and an antigen bound with a primary antibody is then stained (secondary antibody method), or a method in which a label is prepared by directly binding a fluorescent label and biotin and an antigen bound with a primary antibody and avidin or a streptavidin-modified secondary antibody is then stained (biotin-avidin method or sandwich method) can be employed.

Any primary antibody may be used in the immunostaining and the primary antibody is variable depending on the subject to be immunostained. For example, when immunostaining is performed using HER2 as an antigen, an anti-HER2 antibody is used. Further, any secondary antibody may be used and the secondary antibody is variable depending on the primary antibody. Examples thereof include anti-mouse, rabbit, bovine, goat, sheep, dog and chicken antibodies.

For binding of a fluorescent label with an antibody or biotin, any existing method may be employed. For example, amidation by reaction between amine and carboxylic acid, sulfidation by reaction between maleimide and thiol, imination by reaction between aldehyde and amine, or amination by reaction between epoxy and amine can be used.

Here, the above-described immunostaining is not restricted to tissue staining and can be applied to cell staining as well. Further, the biological substance to be detected is not particularly restricted as long as a substance which specifically binds thereto is present. Typically, a combination of an antigen and an antibody is used as described above; however, it is also possible to use, for example, a combination of a nucleic acid molecule (oligonucleotide or polynucleotide) and a nucleic acid molecule having a sequence that can be complementarily coupled thereto.

[Immobilization Step]

The immobilization step performed in the staining method of the present invention is a step of immobilizing the fluorescent label introduced by the above-described immunostaining step onto a biological substance, an antibody bound thereto or the like. By performing a treatment with an immobilization solution, proteins are cross-linked and denatured, so that the fluorescent label can be chemically and physically bound more firmly in a stable state to the biological substance, the antibody bound thereto or the like. In the present invention, such immobilization treatment can be carried out by immersing the stained tissue section obtained by the histochemical staining step in an immobilization solution. For example, the stained tissue section obtained by the histochemical staining step can be immersed in a dilute paraformaldehyde aqueous solution for several minutes to several hours or so.

Examples of an immobilization solution that can be used in the present invention include cross-linking agents and cell membrane permeable substances, such as formalin, paraformaldehyde, glutaraldehyde, acetone, ethanol and methanol. Thereamong, formalin, paraformaldehyde and glutaraldehyde can be preferably used because they are capable of attaining strong immobilization.

[Mounting Step]

The mounting step comprises the dehydration and clearing step using an organic solvent of the subject tissue section and the mounting step using an oil-based mounting medium. In the dehydration and clearing step, after washing the stained tissue section with an aqueous washing solution such as PBS, the tissue section is dehydrated with EtOH (ethanol) and then substituted with xylene. The dehydration with EtOH is carried out by immersing the tissue section sequentially in EtOH whose water content is reduced to, for example, 50%, 30%, 10% and 0% and thereby substituting the tissue section with EtOH. By immersing the thus EtOH-substituted tissue section in xylene, the tissue section is substituted with xylene and cleared. By placing the thus xylene-substituted tissue section on an oil-based mounting medium and putting a cover glass or the like thereon, the tissue section is mounted.

[Mounting Medium]

A mounting medium is constituted by a solvent (mounting solvent) and a resin. In the present invention, as a mounting medium, an oil-based mounting medium (may be generally referred to as "non-aqueous mounting medium") is used. The term "oil-based mounting medium" refers to a mounting medium which comprises a solvent not freely miscible with water.

Here, the phrase "not freely miscible with water" means that the solvent has a volume-based solubility of 15% or less in water.

Further, the mounting medium of the present invention may also contain a discoloration inhibitor. Such a mounting medium is hereinafter referred to as "discoloration inhibitor-containing mounting medium".

The mounting medium may be a commercially available oil-based mounting medium or a mounting medium prepared uniquely. Examples of the commercially available oil-based mounting medium include DPX (manufactured by Sigma-Aldrich; main components: polystyrene polymer=about 21.8%, xylene=about 69.7%), Entellan New (registered trademark, manufactured by Merck KGaA; main components: acrylic resin and xylene=about 60%) and PARA Mount-N (registered trademark, manufactured by FALMA; main components: acrylic resin and aliphatic hydrocarbons). Some of the commercially available oil-based mounting media can be used as is, while others can be used after diluting the product (stock solution) with a prescribed solvent. Alternatively, by dissolving a natural resin such as Canada balsam or a synthetic resin such as polystyrene or polymethyl methacrylate into a mounting solvent, an oil-based mounting medium can be prepared uniquely.

<Mounting Solvent>

In the present invention, as a mounting solvent, a solvent which comprises an organic solvent not freely miscible with water is used. The mounting solvent corresponds to, for example, a solvent contained in the above-described commercially available oil-based mounting media, a solvent prescribed for diluting the commercially available oil-based mounting media, or a solvent used for uniquely preparing an oil-based mounting medium.

The organic solvent not freely miscible with water can be selected from aromatic hydrocarbons, unsaturated hydrocarbons, carbonyl-containing compounds (ketones), esters, ethers and alcohols.

Thereamong, as an aromatic hydrocarbon, for example, benzene, toluene and xylene can be used. As an unsaturated hydrocarbon, for example, limonene and pinene can be used. As a ketone, for example, cyclohexanone and methyl ethyl ketone can be used. As an ester-based organic solvent, for example, butyl acetate can be used. As an ether, for example, anisole, 1,4-di(2-hydroxyethoxy)benzene and ethylene glycol monophenyl ether can be used. As an alcohol, for example, butanol, pentanol and hexanol can be used. Particularly, xylene, toluene and limonene are preferred because of their availability, refractive index of about 1.5, which is close to that of a tissue section, and drying rate of several ten minutes or so, which is operationally suitable.

Any one of the above-described organic solvents not freely miscible with water may be used individually, or a plurality thereof may be used in combination.

Further, the mounting solvent may be constituted only by an organic solvent not freely miscible with water or, as required, in addition to an organic solvent not freely miscible with water, the mounting solvent may also contain water and/or an organic solvent that is freely miscible with water in such an amount that does not inhibit the actions and effects of the present invention. In a mounting medium not freely miscible with water, the ratio (vol %) of the solvent not freely miscible with water that is contained in the mounting solvent is usually 50 to 100%, preferably 70 to 100%, more preferably 90 to 100%. Such a mounting medium that comprises a solvent not freely miscible with water in the prescribed range is preferred not only because the difference between the refractive index thereof and that of a specimen is small, so that the specimen can be made transparent and a permanent preparation showing good color tone and color development in morphological staining can be easily prepared, but also because such a mounting medium can create a more dehydrated condition, so that contamination by water during the preparation of a specimen can be easily inhibited and the specimen can thus be evenly dried.

<Resin>

Since the resin contained in the mounting medium remains as solid after the solvent component is evaporated, as the resin, one which does not adversely affect the observation is suitable. Accordingly, a resin which is highly transparent having a refractive index close to that of glass is appropriate. Further, since coloration and fluorescence adversely affect fluorescence microscopy, it is preferred that the resin have neither of them. The resin used in the present invention is not particularly restricted as long as it satisfies the above-described conditions, and examples thereof include natural resins such as Canada balsam and synthetic resins such as polystyrene and polymethyl methacrylate.

[Discoloration Inhibitor]

As the discoloration inhibitor, one which does not have any problem in terms of the solubility in the mounting solvent comprising a solvent not freely miscible with water can be selected from phenolic, amine-based, phosphorus-based, sulfur-based and unsaturated hydrocarbon-based discoloration inhibitors.

Examples of the phenolic discoloration inhibitors that can be used include phenols that are derived from natural products, such as rutin, catechin, hesperidin, methyl hesperidin, myricitrin, quercetin, morin, fisetin, naringenin, naringin, hesperidin, taxifolin, apigenin, geosmin, luteolin, cyanidin, delphinidin, malvidin, pelargonidin, peonidin, tannin, tocopherol and tocotrienol; and hindered phenols such as p-phenylazophenol, 4-nitroaniline, 2,6-di-tert-butyl-4-hydroxymethylphenol, N,N'-disalicylal-1,2-propanediamine, triethylene glycol-bis[3-(3-t-butyl-5-methyl-4-hydroxyphenyl)propionate], 1,6-hexanediol-bis[3-(3,5-di-t-butyl-4-hydroxyphenyl)propionate], 2,4-bis-(n-octylthio)-6-(4-hydroxy-3,5-di-t-butylanilino)-1,3,5-triazine, pentaerythrityl-tetrakis[3-(3,5-di-t-butyl-4-hydroxyphenyl)propionate], 2,2-thio-diethylene-bis[3-(3,5-di-t-butyl-4-hydroxyphenyl)propionate], octadecyl-3-(3,5-di-t-butyl-4-hydroxyphenyl) propionate, N,N'-hexamethylene-bis(3,5-di-t-butyl-4-hydroxy-hydrocinnamamide), 3,5-di-t-butyl-4-hydroxybenzyl phosphonate diethyl ester, 1,3,5-trimethyl-2,4,6-tris(3,5-di-t-butyl-4-hydroxybenzyl)benzene, tris(3,5-di-t-butyl-4-hydroxybenzyl)isocyanurate, octylated diphenyl amine, 2,4,-bis[(octylthio)methyl]-o-cresol, isooctyl-3-(3,5-di-t-butyl-4-hydroxyphenyl)propionate and 1,3,5-tris(4-t-butyl-3-hydroxy-2,6-dimethylbenzyl)isocyanurate.

Examples of the amine-based discoloration inhibitors that can be used include tertiary amines such as 1,4-diazabicyclo[2.2.2]octane (DABCO); secondary amines such as phenothiazine, bis(2,2,6,6-tetramethyl-4-piperidyl)sebacate and 2,2,6,6-tetramethylpiperidine; and alkaloids such as caffeine.

Examples of the phosphorus-based discoloration inhibitors that can be used include 2-mercaptobenzimidazole, triphenyl phosphite, tris(2-carboxyethyl)phosphine hydrochloride (TCEP HCl), diisodecyl pentaerythritol diphosphite and 9,10-dihydro-9-oxa-10-phosphaphenanthrene-10-oxide.

Examples of the sulfur-based discoloration inhibitors that can be used include sulfides such as didodecyl-3,3'-thiodipropionate and 2,2'-thiodiethanol; disulfides such as dibenzyl disulfide, DL-α-lipoic acid (thioctic acid) and 3,6-dithia-1,8-octanediol; and thiols such as dithiothreitol and octanediol.

Examples of the unsaturated hydrocarbon-based discoloration inhibitors that can be used include carotenes, carotenoids, xanthophylls, ascorbic acid, tocotrienol and unsaturated fatty acid, such as lutein, lycopene, astaxanthin, canthaxanthin, capsanthin, Myxoxanthophyll, zeaxanthin, carotene and retinoic acid.

It is preferred that the above-described discoloration inhibitors comprise at least one selected from the group consisting of phenols and amines. Such discoloration inhibitors can prevent photobleaching more effectively by inhibiting the oxidation of the fluorescent label by active oxygen that causes photobleaching.

Any one of the above-described discoloration inhibitors may be used individually, or a plurality thereof may be used in combination.

In order to prevent any adverse effect in fluorescence microscopy, it is preferred that these discoloration inhibitors show no absorption at a wavelength of 450 to 600 nm and do not emit light at a wavelength of 500 to 700 nm. Absorption of light leads to a reduction in the brightness of the fluorescent label. Further, emission of light leads to an increased noise during fluorescence microscopy. Here, the expression that a discoloration "shows no absorption" means that, when a xylene solution containing the discoloration inhibitor at a concentration of 1 mg/mL is prepared and placed in a 10-mm cell and the absorbance is measured, the absorbance is 0.5 or less at both 450 nm and 600 nm.

In the present invention, from the standpoint of preventing a reduction in the brightness of fluorescent dye(s), the section slide prepared using a mounting medium containing the above-described discoloration inhibitor(s) is preferably transparent. The term "transparent" used herein means that the absorbance of the prepared section slide is measured to be 0.1 or less at both 450 nm and 600 nm.

[Fluorescence Observation Step]

By irradiating the pathological specimen subjected to immunostaining and morphological staining in the above-described steps with an excitation light having a wavelength appropriate for the fluorescent label in use, the fluorescence emitted by the fluorescent label is observed. By this step, a prescribed biomolecule existing in the pathological specimen can be detected and this information can be utilized to determine, for example, the appropriateness of applying an antibody pharmaceutical (e.g., Herceptin which targets HER2).

For the irradiation of excitation light, the same irradiation means as the one used in an ordinary fluorescence observation may be employed. For example, from a laser light source installed in a fluorescence microscope, an excitation light having an appropriate wavelength and output may be irradiated to the stained pathological specimen using, as required, a filter which selectively allows light having a prescribed wavelength to pass therethrough.

Observation of fluorescence may be performed either through the lens barrel of a fluorescence microscope or on a separate display means (e.g., a monitor) showing an image taken by a camera mounted on a fluorescence microscope. Depending on the fluorescent substance, even when the fluorescence cannot be adequately observed visually through the lens barrel of a fluorescence microscope, the fluorescence may be observed on an image taken by a camera in some cases. As required, a filter which selectively allows light having a prescribed wavelength to pass therethrough may also be used.

Here, in the present invention, there are cases where immunostaining and morphological staining are both performed on the same pathological specimen. When observing an image produced by the morphological staining, it is not required to irradiate the pathological specimen with excitation light for exciting the fluorescent label used in the immunostaining and the image may be observed under the same observation conditions as those of a light microscope.

Therefore, the fluorescence observation can be performed after irradiating excitation light for an arbitrary time; however, the fluorescence observation is performed preferably within 90 minutes after initiating the irradiation of excitation light, more preferably within 30 minutes after initiating the irradiation of excitation light, under normal irradiation conditions (e.g., irradiation energy).

It is desired that the brightness of the fluorescent label should not change before and after the observation under a fluorescence microscope. In the present invention, under observation conditions where an ordinary fluorescence microscope has its diaphragm fully opened and is used at a magnification of ×40, the fluorescent label retains 70% of the pre-irradiation brightness after being irradiated for 30 minutes. With the brightness reduction being in this range, the biological substance detection method is deemed to have certain reliability and can thus be applied to observation of fluorescent immunostaining.

[Kit]

The biological substance detection kit of the present invention is used for the biological substance detection method of the present invention which comprises the above-described steps. The biological substance detection kit of the present invention comprises the above-described mounting medium containing a solvent not freely miscible with water, or the above-described mounting medium containing a solvent not freely miscible with water and a discoloration inhibitor. The biological substance detection kit of the present invention may further comprise: an instruction manual which describes the biological substance detection method according to the present invention as an instruction; a fluorescent label for immunostaining; and a fluorescent labeling reagent.

The fluorescent label for immunostaining to be included in the kit can be selected from those fluorescent labels that are described in the above section [Fluorescent Label for Immunostaining]. As the fluorescent labeling reagent, any of those substances that are described in the above section [Immunostaining Step], for example, a primary antibody or a secondary antibody, can be selected. The mounting medium is the same as the one described in the above section [Mounting Medium], and the solvent and resin that constitute the mounting medium can each be selected from those solvents and resins that are described in the above sections [Mounting Solvent] and [Resin], respectively. The discoloration inhibitor can be selected from those discoloration inhibitors that are described in the above section [Discoloration Inhibitor].

<Instruction Manual>

The instruction manual to be included in the kit is one which describes any one of the biological substance detection methods according to the present invention as an instruction for carrying out the method according to the present invention. The instruction manual takes any specific embodiment as long as it can properly convey the above-described information. For example, the instruction manual may be printed on a piece of paper, the package of the kit, or the label of a constituent of the kit. Alternatively, the instruction manual may be recorded on a computer-readable medium such as a CD.

EXAMPLES

The present invention will now be described in detail by way of examples thereof; however, the present invention is not restricted to the following examples.

<Preparation of Fluorescent Labels>

The fluorescent labels were all prepared in a streptavidin-bound form.

(Fluorescent Label 1: Texas Red Dye)

As a fluorescent dye, Sulforhodamine 101 acid chloride (Texas Red dye, manufactured by Dojinsha Co., Ltd.) was used. Streptavidin was bound to the fluorescent dye as follows.

Texas Red dye was adjusted with PBS (phosphate-buffered physiological saline) containing 2 mM of EDTA (ethylenediamine tetraacetic acid) to a concentration of 3 nM. The resulting solution was mixed with SM(PEG)12 (manufactured by Thermo Fisher Scientific K.K.; succinimidyl-[(N-maleimidopropionamido)-dodecaethylene glycol]ester) to a final concentration of 10 mM and allowed to react for 1 hour. The thus obtained mixture was centrifuged at 10,000 G for 20 minutes and the resulting supernatant was removed. Then, PBS containing 2 mM of EDTA was added to disperse the precipitates and the resulting dispersion was centrifuged again. The precipitates were washed three times by the same procedure to obtain fluorescent dye-containing nanoparticles having a maleimide group at a terminal (The unit M represents molar concentration, mol/L).

Meanwhile, streptavidin (manufactured by Wako Pure Chemical Industries, Ltd.) was subjected to a thiol group addition treatment with N-succinimidyl-5-acetylthioacetate (SATA) and then filtered through a gel-filtration column to obtain a solution of streptavidin capable of binding to dye-containing nanoparticles.

The above-described Texas Red dye and streptavidin were mixed in PBS containing 2 mM of EDTA and allowed to react for 1 hour. Then, the reaction was terminated with an addition of 10 mM mercaptoethanol. After concentrating the resulting solution using a centrifugation filter, unreacted streptavidin and the like were removed using a gel-filtration column for purification, thereby obtaining a streptavidin-bound Texas Red dye.

(Fluorescent Label 2: Perylene Dye)

Perylene diimide, which was used as a fluorescent dye, was prepared by the following method. N,N'-bis(2,6-diisopropylphenyl)-1,6,7,12-tetraphenoxyperylene-3,4:9,10-tetracarboxdiimide was treated with concentrated sulfuric acid to prepare a perylene diimide sulfonic acid derivative. This was then converted to an acid chloride to obtain a perylene diimide sulfonic acid chloride derivative. A streptavidin-bound dye was obtained in the same manner as the fluorescent dye 1, except that the thus obtained perylene diimide sulfonic acid chloride derivative was used.

(Fluorescent Label 3: Texas Red Dye-Containing Melamine Nanoparticle)

After adding 2.5 mg Sulforhodamine 101 (manufactured by Sigma-Aldrich) to 22.5 mL of water, the resulting mixture was heated at 70° C. for 20 minutes on a hot stirrer and 1.5 g of a melamine resin, Nikalac MX-035 (manufactured by Nippon Carbide Industries Co., Ltd.), was added thereto, followed by heating of the resultant with stirring for another 5 minutes. Then, 100 µL of formic acid was further added and the resultant was heated with stirring at 60° C. for 20 minutes and subsequently cooled to room temperature. Thereafter, the resulting reaction mixture was placed in a centrifugal tube and centrifuged at 12,000 rpm for 20 minutes, followed by removal of the resulting supernatant. The precipitates were washed with ethanol and water.

Then, 0.1 mg of the thus obtained particles were dispersed in 1.5 mL of EtOH and 2 µL of aminopropyltrimethoxysilane, LS-3150 (manufactured by Shin-Etsu Chemical Co., Ltd.), was added thereto. The resulting mixture was allowed to react for 8 hours so as to perform surface amination treatment.

The thus obtained dye-containing nanoparticles were adjusted with PBS (phosphate-buffered physiological saline) containing 2 mM of EDTA (ethylenediamine tetraacetic acid) to a concentration of 3 nM. The resulting solution was mixed with SM(PEG)12 (manufactured by Thermo Fisher Scientific K.K.; succinimidyl-[(N-maleimidopropionamido)-dodecaethylene glycol]ester) to a final concentration of 10 mM and allowed to react for 1 hour. The thus obtained mixture was centrifuged at 10,000 G for 20 minutes and the resulting supernatant was removed. Then, PBS containing 2 mM of EDTA was added to disperse the precipitates and the resulting dispersion was centrifuged again. The precipitates were washed three times by the same procedure to obtain fluorescent dye-containing nanoparticles having a maleimide group at a terminal.

Meanwhile, streptavidin (manufactured by Wako Pure Chemical Industries, Ltd.) was subjected to a thiol group addition treatment with N-succinimidyl-5-acetylthioacetate (SATA) and then filtered through a gel-filtration column to obtain a solution of streptavidin capable of binding to dye-containing nanoparticles.

The above-described fluorescent nanoparticles and streptavidin were mixed in PBS containing 2 mM of EDTA and allowed to react for 1 hour. Then, the reaction was terminated with an addition of 10 mM mercaptoethanol. After concentrating the resulting solution using a centrifugation filter, unreacted streptavidin and the like were removed using a gel-filtration column for purification, thereby obtaining melamine nanoparticles containing streptavidin-bound Texas Red dye.

(Fluorescent Label 4: Perylene Dye-Containing Melamine Nanoparticle)

The perylene diimide sulfonic acid chloride derivative described above as the dye 2 was used as a fluorescent dye.

Except this, melamine nanoparticles containing streptavidin-bound perylene dye were obtained in the same manner as the above-described fluorescent dye 3.

(Fluorescent Label 5: FITC Dye-Containing Melamine Nanoparticle)

Melamine nanoparticles containing streptavidin-bound FITC dye were obtained in the same manner as the above-described fluorescent dye 3, except that fluorescein isothiocyanate (FITC, manufactured by Dojinsha Co., Ltd.) was used as the fluorescent dye.

(Fluorescent Label 6: Texas Red Dye-Containing Silica Nanoparticle)

In DMF, 3.4 mg of the Texas Red dye used in the fluorescent label 1 and 3 µL of 3-aminopropyltrimethoxysilane (KBM903, manufactured by Shin-Etsu Chemical Co., Ltd.) were mixed to obtain an organoalkoxysilane compound. Subsequently, 0.6 mL of the thus obtained organoalkoxysilane compound was mixed for 3 hours with 48 mL of ethanol, 0.6 mL of TEOS (tetraethoxysilane), 2 mL of water and 2 mL of 28% aqueous ammonia. The mixture produced in the above-described step was centrifuged at 10,000 G for 20 minutes and the resulting supernatant was removed. Then, ethanol was added to disperse the precipitates and the resulting dispersion was centrifuged again. The precipitates were washed twice by the same procedure with ethanol and pure water, thereby obtaining Texas Red dye-containing silica nanoparticles.

The thus obtained dye-containing nanoparticles were adjusted with PBS (phosphate-buffered physiological saline) containing 2 mM of EDTA (ethylenediamine tetraacetic acid) to a concentration of 3 nM. The resulting solution was mixed with SM(PEG)12 (manufactured by Thermo Fisher Scientific K.K.; succinimidyl-[(N-maleimidopropionamido)-dodecaethylene glycol]ester) to a final concentration of 10 mM and allowed to react for 1 hour. The thus obtained mixture was centrifuged at 10,000 G for 20 minutes and the resulting supernatant was removed. Then, PBS containing 2 mM of EDTA was added to disperse the precipitates and the resulting dispersion was centrifuged again. The precipitates were washed three times by the same procedure to obtain fluorescent dye-containing nanoparticles having a maleimide group at a terminal.

Meanwhile, streptavidin (manufactured by Wako Pure Chemical Industries, Ltd.) was subjected to a thiol group addition treatment with N-succinimidyl-5-acetylthioacetate (SATA) and then filtered through a gel-filtration column to obtain a solution of streptavidin capable of binding to dye-containing nanoparticles.

The above-described fluorescent nanoparticles and streptavidin were mixed in PBS containing 2 mM of EDTA and allowed to react for 1 hour. Then, the reaction was terminated with an addition of 10 mM mercaptoethanol. After concentrating the resulting solution using a centrifugation filter, unreacted streptavidin and the like were removed using a gel-filtration column for purification, thereby obtaining silica nanoparticles containing streptavidin-bound Texas Red dye.

(Fluorescent Label 7: Perylene Dye-Containing Silica Nanoparticle)

Silica nanoparticles containing streptavidin-bound perylene dye were obtained in the same manner as the above-described fluorescent dye 6, except that perylene diimide used in the fluorescent label 2 was used as the fluorescent dye.

(Fluorescent Label 8: FITC Dye-Containing Silica Nanoparticle)

Silica nanoparticles containing streptavidin-bound FITC dye were obtained in the same manner as the above-described fluorescent dye 6, except that FITC used in the fluorescent dye 3 was used as the fluorescent dye.

(Fluorescent Label 9: Texas Red Dye-Containing Polystyrene Nanoparticle)

Texas Red dye-containing polystyrene particles were prepared by a soap-free emulsion polymerization method. A fluorescent dye, Sulforhodamine 101 acid chloride (Texas Red dye, manufactured by Dojinsha Co., Ltd.), was mixed with 4-aminostyrene (manufactured by Tokyo Chemical Industry Co., Ltd.) at room temperature for 1 hour to prepare dye-bound styrene. To 5 mL of pure water deaerated by argon bubbling, 0.18 g of glycidyl methacrylate (manufactured by Tokyo Chemical Industry Co., Ltd.), 0.05 g of styrene (manufactured by Wako Pure Chemical Industries, Ltd.), 0.05 g of divinylbenzene and 0.005 g of the thus obtained dye-bound styrene were added. After heating the resultant with stirring to 70° C., 0.012 g of a water-soluble azo polymerization initiator, V-50 (manufactured by Wako Pure Chemical Industries, Ltd.), was added and the resulting mixture was allowed to react for 12 hours. The resulting reaction solution was centrifuged at 10,000 G for 20 minutes to recover particles. The recovered particles were purified by dispersing them in pure water and then centrifuging the resulting dispersion once again for recovery. The thus obtained particles were added to an excess amount of aqueous ammonia so as to convert the epoxy groups at the particle terminals into amino groups, thereby obtaining dye-containing polystyrene nanoparticles having an amino group at a terminal.

The thus obtained dye-containing nanoparticles were adjusted with PBS (phosphate-buffered physiological saline) containing 2 mM of EDTA (ethylenediamine tetraacetic acid) to a concentration of 3 nM. The resulting solution was mixed with SM(PEG)12 (manufactured by Thermo Fisher Scientific K.K.; succinimidyl-[(N-maleimidopropionamido)-dodecaethylene glycol]ester) to a final concentration of 10 mM and allowed to react for 1 hour. The thus obtained mixture was centrifuged at 10,000 G for 20 minutes and the resulting supernatant was removed. Then, PBS containing 2 mM of EDTA was added to disperse the precipitates and the resulting dispersion was centrifuged again. The precipitates were washed three times by the same procedure to obtain fluorescent dye-containing nanoparticles having an amino group at a terminal.

Meanwhile, streptavidin (manufactured by Wako Pure Chemical Industries, Ltd.) was subjected to a thiol group addition treatment with N-succinimidyl-5-acetylthioacetate (SATA) and then filtered through a gel-filtration column to obtain a solution of streptavidin capable of binding to dye-containing nanoparticles.

The above-described fluorescent nanoparticles and streptavidin were mixed in PBS containing 2 mM of EDTA and allowed to react for 1 hour. Then, the reaction was terminated with an addition of 10 mM mercaptoethanol. After concentrating the resulting solution using a centrifugation filter, unreacted streptavidin and the like were removed using a gel-filtration column for purification, thereby obtaining polystyrene nanoparticles containing streptavidin-bound Texas Red dye.

(Fluorescent Label 10: Perylene Dye-Containing Polystyrene Nanoparticle)

Polystyrene nanoparticles containing streptavidin-bound perylene dye were obtained in the same manner as the above-described fluorescent dye 9, except that perylene diimide used in the fluorescent label 2 was used as the fluorescent dye.

(Fluorescent Label 11: FITC Dye-Containing Polystyrene Nanoparticle)

Polystyrene nanoparticles containing streptavidin-bound FITC dye were obtained in the same manner as the above-described fluorescent dye 9, except that FITC used in the fluorescent dye 3 was used as the fluorescent dye.

(Fluorescent Label 12: CdSe)

Carboxylic acid-terminated CdSe/ZnS (Qdot 605, manufactured by Invitrogen) was used as fluorescent nanoparticle. The fluorescent nanoparticles were activated by EDTA (manufactured by Thermo Fisher Scientific K.K.) and then bound with streptavidin in the same manner as the fluorescent label 1, thereby obtaining streptavidin-bound fluorescent nanoparticles.

(Fluorescent Label 13: CdSe-Containing Nanoparticle)

To 10 μL of CdSe/ZnS decane dispersion (Qdot 605, manufactured by Invitrogen), 0.1 mg of TEOS, 0.01 mL of ethanol and 0.03 mL of concentrated aqueous ammonia were added, and the resultant was stirred for 3 hours to perform hydrolysis. The thus obtained mixture was centrifuged at 10,000 G for 20 minutes and the resulting supernatant was removed. Then, ethanol was added to disperse the precipitates and the resulting dispersion was centrifuged again. The precipitates were washed twice by the same procedure with ethanol and pure water, thereby obtaining 60 mg of CdSe-containing nanoparticles.

By SEM observation of 1,000 of the thus obtained CdSe-containing nanoparticles, the average particle size and the variation coefficient were found to be 108 nm and 14%, respectively.

The thus obtained CdSe-containing nanoparticles were subjected to surface amination, PEGylation and modification with streptavidin in the same manner as in the method of preparing the fluorescent dye 3, thereby obtaining streptavidin-bound CdSe-containing nanoparticles.

The list of the fluorescent labels used is shown in Table 1.

TABLE 1

| Fluorescent label | Type of fluorescent label | Dye or nanoparticle composition | Contained particle matrix |
|---|---|---|---|
| Fluorescent label 1 | Fluorescent dye | Texas Red | none |
| Fluorescent label 2 | Fluorescent dye | perylene | none |
| Fluorescent label 3 | Fluorescent dye-containing particle | Texas Red | melamine |
| Fluorescent label 4 | Fluorescent dye-containing particle | perylene | melamine |
| Fluorescent label 5 | Fluorescent dye-containing particle | fluorescein | melamine |
| Fluorescent label 6 | Fluorescent dye-containing particle | Texas Red | silica |
| Fluorescent label 7 | Fluorescent dye-containing particle | perylene | silica |
| Fluorescent label 8 | Fluorescent dye-containing particle | fluorescein | silica |
| Fluorescent label 9 | Fluorescent dye-containing particle | Texas Red | polystyrene |
| Fluorescent label 10 | Fluorescent dye-containing particle | perylene | polystyrene |
| Fluorescent label 11 | Fluorescent dye-containing particle | fluorescein | polystyrene |
| Fluorescent label 12 | Fluorescent nanoparticle | CdSe | none |
| Fluorescent label 13 | Fluorescent nanoparticle-containing particle | CdSe | silica |

<Preparation of Mounting Medium>

As mounting media, the following mounting media 1-1 to 1-10, 2-1 to 2-5 and 3-1 were prepared.

[Discoloration Inhibitor-Containing Mounting Media]

Mounting Medium 1-1: Rutin-Containing Mounting Medium

As a mounting medium, Entellan New (manufactured by Merck KGaA; main components: acrylic resin and xylene=about 60%) or PARA Mount-N (manufactured by FALMA; main components: acrylic resin and aliphatic hydrocarbons) was used as is without diluting the purchased form.

To the mounting medium, rutin was added as a discoloration inhibitor in an amount of 1% by weight (hereinafter, abbreviated as "wt %"), and the resulting mixture was stirred to obtain a discoloration inhibitor-containing mounting medium.

Mounting Medium 1-2: 2,6-di-tert-butyl-4-hydroxymethylphenol-Containing Mounting Medium As a mounting medium, Entellan New (manufactured by Merck KGaA) or PARA Mount-N (manufactured by FALMA) was used. To the mounting medium, 2,6-di-tert-butyl-4-hydroxymethylphenol was added as a discoloration inhibitor in an amount of 1 wt %, and the resulting mixture was stirred to obtain a discoloration inhibitor-containing mounting medium.

Mounting Medium 1-3: bis(2,2,6,6-tetramethyl-4-piperidyl)sebacate-Containing Mounting Medium As a mounting medium, Entellan New (manufactured by Merck KGaA) or PARA Mount-N (manufactured by FALMA) was used. To the mounting medium, bis(2,2,6,6-tetramethyl-4-piperidyl)sebacate was added as a discoloration inhibitor in an amount of 1 wt %, and the resulting mixture was stirred to obtain a discoloration inhibitor-containing mounting medium.

Mounting Medium 1-4: Phenothiazine-Containing Mounting Medium

As a mounting medium, Entellan New (manufactured by Merck KGaA) or PARA Mount-N (manufactured by FALMA) was used. To the mounting medium, phenothiazine was added as a discoloration inhibitor in an amount of 1 wt %, and the resulting mixture was stirred to obtain a discoloration inhibitor-containing mounting medium.

Mounting Medium 1-5: 2-Mercaptobenzimidazole

As a mounting medium, Entellan New (manufactured by Merck KGaA) or PARA Mount-N (manufactured by FALMA) was used. To the mounting medium, 2-mercaptobenzimidazole was added as a discoloration inhibitor in an amount of 1 wt %, and the resulting mixture was stirred to obtain a discoloration inhibitor-containing mounting medium.

Mounting Medium 1-6: Triphenyl Phosphite-Containing Mounting Medium

As a mounting medium, Entellan New (manufactured by Merck KGaA) or PARA Mount-N (manufactured by FALMA) was used. To the mounting medium, triphenyl phosphite was added as a discoloration inhibitor in an amount of 1 wt %, and the resulting mixture was stirred to obtain a discoloration inhibitor-containing mounting medium.

Mounting Medium 1-7: Dibenzyl Disulfide-Containing Mounting Medium

As a mounting medium, Entellan New (manufactured by Merck KGaA) or PARA Mount-N (manufactured by FALMA) was used. To the mounting medium, dibenzyl disulfide was added as a discoloration inhibitor in an amount of 1 wt %, and the resulting mixture was stirred to obtain a discoloration inhibitor-containing mounting medium.

Mounting Medium 1-8: didodecyl-3,3'-thiodipropionate-Containing Mounting Medium

As a mounting medium, Entellan New (manufactured by Merck KGaA) or PARA Mount-N (manufactured by FALMA) was used. To the mounting medium, didodecyl-3,3'-thiodipropionate was added as a discoloration inhibitor in an amount of 1 wt %, and the resulting mixture was stirred to obtain a discoloration inhibitor-containing mounting medium.

Mounting Medium 1-9: DL-α-Lipoic Acid-Containing Mounting Medium

As a mounting medium, Entellan New (manufactured by Merck KGaA) or PARA Mount-N (manufactured by FALMA) was used. To the mounting medium, DL-α-lipoic acid was added as a discoloration inhibitor in an amount of 1 wt %, and the resulting mixture was stirred to obtain a discoloration inhibitor-containing mounting medium.

Mounting Medium 1-10: Retinoic Acid-Containing Mounting Medium

As a mounting medium, Entellan New (manufactured by Merck KGaA) or PARA Mount-N (manufactured by FALMA) was used. To the mounting medium, retinoic acid was added as a discoloration inhibitor in an amount of 1 wt %, and the resulting mixture was stirred to obtain a discoloration inhibitor-containing mounting medium.

Mounting Medium 2-1: Mounting Medium Containing No Discoloration Inhibitor

As a mounting medium, Entellan New (manufactured by Merck KGaA) or PARA Mount-N (manufactured by FALMA) was used as is. No discoloration inhibitor was added thereto.

Mounting Medium 2-2: Cyanidin-Containing Mounting Medium

To the mounting medium, cyanidin was added as a discoloration inhibitor in an amount of 1 wt %, and the resulting mixture was stirred to obtain a discoloration inhibitor-containing mounting medium.

Mounting Medium 2-3: p-Phenylazophenol-Containing Mounting Medium

To the mounting medium, p-phenylazophenol was added as a discoloration inhibitor in an amount of 1 wt %, and the resulting mixture was stirred to obtain a discoloration inhibitor-containing mounting medium.

Mounting Medium 2-4: 4-Nitroaniline-Containing Mounting Medium

As a mounting medium, Entellan New (manufactured by Merck KGaA) or PARA Mount-N (manufactured by FALMA) was used. To the mounting medium, 4-nitroaniline was added as a discoloration inhibitor in an amount of 1 wt %, and the resulting mixture was stirred to obtain a discoloration inhibitor-containing mounting medium.

Mounting Medium 2-5: Lycopene-Containing Mounting Medium

As a mounting medium, Entellan New (manufactured by Merck KGaA) or PARA Mount-N (manufactured by FALMA) was used. To the mounting medium, lycopene was added as a discoloration inhibitor in an amount of 1 wt %, and the resulting mixture was stirred to obtain a discoloration inhibitor-containing mounting medium.

Mounting Medium 3-1: DABCO-Containing Aqueous Mounting Medium

As a mounting medium, Fluoromount (manufactured by Cosmo Bio Co., Ltd.; aqueous mounting medium) was used. To this mounting medium, 1,4-diazabicyclo[2.2.2]octane (DABCO) was added as a discoloration inhibitor in an amount of 1 wt %, and the resulting mixture was stirred to obtain a discoloration inhibitor-containing mounting medium.

The list of the mounting media used is shown in Table 2.

TABLE 2

| Mounting medium | Classification of discoloration inhibitor contained in mounting medium | Discoloration inhibitor |
| --- | --- | --- |
| Mounting medium1-1 | phenolic discoloration inhibitor | rutin |

TABLE 2-continued

| Mounting medium | Classification of discoloration inhibitor contained in mounting medium | Discoloration inhibitor |
|---|---|---|
| Mounting medium1-2 | phenolic discoloration inhibitor | 2,6-di-tert-butyl-4-hydroxymethylphenol |
| Mounting medium1-3 | amine-based discoloration inhibitor | bis(2,2,6,6-tetramethyl-4-piperidyl)sebacate |
| Mounting medium1-4 | amine-based discoloration inhibitor | phenothiazine |
| Mounting medium1-5 | phosphorus-based discoloration inhibitor | 2-mercaptobenzimidazole |
| Mounting medium1-6 | phosphorus-based discoloration inhibitor | triphenyl phosphite |
| Mounting medium1-7 | sulfur-based discoloration inhibitor | dibenzyl disulfide |
| Mounting medium1-8 | sulfur-based discoloration inhibitor | didodecyl-3,3'-thiodipropionate |
| Mounting medium1-9 | sulfur-based discoloration inhibitor | DL-α-lipoic acid |
| Mounting medium1-10 | unsaturated hydrocarbon-based discoloration inhibitor | retinoic acid |
| Mounting medium2-1 | — | none |
| Mounting medium2-2 | phenolic discoloration inhibitor | cyanidin |
| Mounting medium2-3 | phenolic discoloration inhibitor | p-phenylazophenol |
| Mounting medium2-4 | amine-based discoloration inhibitor | 4-nitroaniline |
| Mounting medium2-5 | unsaturated hydrocarbon-based discoloration inhibitor | lycopene |
| Mounting medium3-1 | amine-based discoloration inhibitor | 1,4-diazabicyclo[2.2.2]octane (DABCO) |

<Tissue Staining Step>

[Tissue Immunostaining]

Using the fluorescent labels 1 to 13, human breast tissue was immunostained. As a section to be stained, a tissue array slide manufactured by Cosmo Bio Co., Ltd. (CB-A712) was used. After subjecting the tissue array slide to a deparaffinization treatment, an antigen activation treatment was performed by subjecting the tissue array slide to displacement washing with water and a 15-minute autoclave treatment in 10 mM citrate buffer (pH 6.0). Thereafter, the tissue array slide was washed with PBS buffer and then subjected to a 1-hour blocking treatment with 1% BSA-containing PBS buffer in a moist chamber. After the blocking treatment, the tissue section was allowed to react for 2 hours with biotinylated trastuzumab diluted with 1% BSA-containing PBS buffer to a concentration of 0.05 nM, and the resulting tissue section was subsequently washed. The tissue section was further allowed to react with the respective fluorescent labels 1 to 13 for 0.5 hour and then washed, thereby obtaining an immunohistochemically-stained section. The thus obtained immunohistochemically-stained section was then immersed in 4% neutral paraformaldehyde aqueous buffer for 10 minutes to perform an immobilization treatment.

[Morphological Staining]

The thus immobilized immunohistochemically-stained section was subjected to HE staining and then immersed in ethanol for dehydration. The dehydrated section was cleared by further immersing the section in xylene and air-drying the resulting section, thereby a double-stained section was obtained. It is noted here that the HE staining performed as morphological staining does not have any effect on the below-described evaluation of light resistance.

[Mounting]

Subsequently, the thus morphologically-stained section was mounted. In this process, the fluorescent labels 1 to 13 and the mounting media 1-1 to 1-10, 2-1 to 2-5 and 3-1 were each used.

<Evaluations of Tissue Sample>

[Evaluation 1: Absorption by Discoloration Inhibitor]

For the evaluation of absorption by a discoloration inhibitor, a xylene solution containing the discoloration inhibitor at a concentration of 1 mg/mL was prepared and placed in a 10-mm cell and the absorbance was measured. When the absorbance was 0.5 or less at both 450 nm and 600 nm, the absorption by the discoloration inhibitor was evaluated as "absent" and, when the absorbance was higher than 0.5 at either or both of these wavelengths, the absorption by the discoloration inhibitor was evaluated as "present". For the measurement of the absorbance, a spectrophotometer, U-4100 manufactured by Hitachi, Ltd., was used. It is noted here that, when the solubility of the subject discoloration inhibitor in xylene was poor, a 0.5-wt % xylene solution of the discoloration inhibitor was prepared and placed in a 10-mm cell to carryout the measurement. When the solubility in xylene was even worse, the solvent was changed to a mixed solvent of xylene and EtOH or the like to carry out the measurement.

[Evaluation 2: Evaluation of Light Resistance Before and after 30-Minute Irradiation, and Improvement Rate]

The tissue sections that were immunostained with the respective fluorescent labels 1 to 13 and then mounted with the respective mounting media 1-1 to 1-10 and 2-1 to 2-5 were each allowed to emit fluorescence by irradiation with excitation light. For each of the resulting tissue sections, an image was obtained using an upright-type fluorescence microscope (manufactured by Carl Zeiss; Axio Imager 2 equipped with a monochrome camera, AxioCam MRm).

The excitation wavelength (nm) and the fluorescence wavelength (nm) were set using an optical filter. For Texas Red, perylene imide and those nanoparticles containing Texas Red or perylene imide, the excitation wavelength and the fluorescence wavelength were set to be 575 to 600 nm and 612 to 682 nm, respectively. For fluorescein and the fluorescein-containing nanoparticles, the excitation wavelength and the fluorescence wavelength were set to be 450 to 490 nm and 500 to 550 nm, respectively. Further, for CdSe and the CdSe-containing nanoparticles, the excitation wavelength and the fluorescence wavelength were set to be 345 to 395 nm and 600 to 700 nm, respectively.

The conditions of the excitation wavelength in the microscope observation and image acquisition were set such that the intensity of the irradiation light in the vicinity of the center of the visual field was 900 W/cm$^2$ for excitation at 575 to 600 nm and 450 to 490 nm, and 500 W/cm$^2$ for excitation at 365 nm and 345 to 395 nm. Here, the intensity of the irradiation light was determined by measuring the light energy value using a power meter equipped with a ×40 objective lens, 8230 manufactured by Advantest Corporation, and then dividing the measured value by the irradiated visual area of the ×40 objective lens (about φ50 μm). In the image acquisition process, the exposure time was arbitrarily set such that the image brightness was not saturated. The measurement was performed at an exposure time of, for example, 1,000 ms. It is noted here that the acquired images were not corrected and the brightness value was adjusted to be linear over the entire range.

The brightness of each pixel was calculated from the thus obtained respective images using an image analysis software, Image-J (manufactured by the U.S. National Institutes of Health), and the average brightness of the sites that were stained with each fluorescent label (immunostained parts) was calculated (brightness of the immunostained parts). This average brightness corresponds to a signal value (S). In the 256-gradation data, a brightness of "0" is defined as black (the darkest) and a brightness of "255" is defined as white (the brightest). When an image having more than 256 color gradations was used, the calculated brightness value was divided by the maximum gradation value and then multiplied by 255 so that the brightness can be compared in terms of 256-gradation scale.

The light resistance of each fluorescent label was evaluated by continuing the irradiation of excitation light with the visual field being fixed for 30 minutes, determining the brightness of the immunostained parts from both of the micrographs that were taken immediately after the start of the irradiation (at the start of the irradiation, 0 minute) and after the irradiation (30 minutes), and then calculating the brightness retention rate (%), which is represented by an equation: (brightness after 30-minute irradiation)/(brightness immediately after the start of irradiation)×100.

Further, for comparison of the effects of the discoloration inhibitors, the same operations were performed using the corresponding mounting media containing no discoloration inhibitor and the improvement rate, which is represented by an equation: (brightness retention rate with the discoloration inhibitor)/(brightness retention rate without the discoloration inhibitor)×100, was calculated.

[Evaluation 3: Storage Property]

For each of the mounted section slides, the brightness after 3-month storage was evaluated. The evaluation of the brightness was performed in the same manner as Evaluation 2. The storage property was evaluated as "○" (present) when 70% or more of the initial brightness was retained, and it was evaluated as "x" (absent) when the brightness was reduced to less than 70% of the initial brightness.

[Evaluation 4: Transparency]

For each of the mounted section slides, using a spectrophotometer U-4100 (manufactured by Hitachi, Ltd.), the absorbance at 450 to 600 nm was measured and evaluated. An evaluation of "○" (transparent) was given when the absorbance was 0.1 or less at both 450 nm and 600 nm, and an evaluation of "x" (non-transparent) was given when the absorbance was higher than 0.1 at either or both of these wavelengths. When the mounting medium is colored, the transparency is reduced. In addition, when the tissue section develops cloudiness, the transparency is also reduced. Thus, from the standpoint of maintaining the brightness of the fluorescent label, it is preferred that the section slide be transparent.

[Evaluation 5: Stain Retainability]

In order to confirm that each tissue section was stained with the respective oil-based mounting media, a sample of each tissue section not subjected to the immobilization step at the time of staining was prepared and compared with the section sample that was subjected to the immobilization step. Comparing against the sample not subjected to the immobilization step, when the initial brightness was increased to 1.1-fold or higher, the fluorescent staining properties were evaluated as "○" (maintained) and, when the initial brightness was reduced to less than 1.1-fold, the fluorescent staining properties were evaluated as "x" (not maintained).

The results of the above-described evaluations are shown in Tables 3-1 to 3-7, 4, 5-1 to 5-3 and 6.

TABLE 3-1

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 1 | En | 1 | done | rutin | absent | 58 | 383 | ○ | ○ | ○ |
| Example 2 | En | 1 | done | 2,6-di-tert-butyl-4-hydroxymethylphenol | absent | 53 | 355 | ○ | ○ | ○ |
| Example 3 | En | 1 | done | bis(2,2,6,6-tetramethyl-4-piperidyl)sebacate | absent | 52 | 344 | ○ | ○ | ○ |
| Example 4 | En | 1 | done | phenothiazine | absent | 49 | 327 | ○ | ○ | ○ |
| Example 5 | En | 1 | done | 2-mercaptobenzimidazole | absent | 43 | 284 | ○ | ○ | ○ |
| Example 6 | En | 1 | done | triphenyl phosphite | absent | 44 | 291 | ○ | ○ | ○ |
| Example 7 | En | 1 | done | dibenzyl disulfide | absent | 41 | 270 | ○ | ○ | ○ |
| Example 8 | En | 1 | done | didodecyl-3,3'-thiodipropionate | absent | 42 | 277 | ○ | ○ | ○ |
| Example 9 | En | 1 | done | DL-α-lipoic acid | absent | 39 | 263 | ○ | ○ | ○ |
| Example 10 | En | 1 | done | retinoic acid | absent | 41 | 270 | ○ | ○ | ○ |
| Example 11 | En | 2 | done | rutin | absent | 65 | 217 | ○ | ○ | ○ |
| Example 12 | En | 2 | done | 2,6-di-tert-butyl-4-hydroxymethylphenol | absent | 62 | 205 | ○ | ○ | ○ |
| Example 13 | En | 2 | done | bis(2,2,6,6-tetramethyl-4-piperidyl)sebacate | absent | 60 | 200 | ○ | ○ | ○ |
| Example 14 | En | 2 | done | phenothiazine | absent | 58 | 193 | ○ | ○ | ○ |
| Example 15 | En | 2 | done | 2-mercaptobenzimidazole | absent | 53 | 176 | ○ | ○ | ○ |
| Example 16 | En | 2 | done | triphenyl phosphite | absent | 54 | 179 | ○ | ○ | ○ |
| Example 17 | En | 2 | done | dibenzyl disulfide | absent | 51 | 170 | ○ | ○ | ○ |
| Example 18 | En | 2 | done | didodecyl-3,3'-thiodipropionate | absent | 52 | 173 | ○ | ○ | ○ |
| Example 19 | En | 2 | done | DL-α-lipoic acid | absent | 50 | 167 | ○ | ○ | ○ |

TABLE 3-1-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 20 | En | 2 | done | retinoic acid | absent | 51 | 170 | ○ | ○ | ○ |

En: Entellan New

TABLE 3-2

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 21 | En | 3 | done | rutin | absent | 65 | 217 | ○ | ○ | ○ |
| Example 22 | En | 3 | done | 2,6-di-tert-butyl-4-hydroxymethylphenol | absent | 62 | 205 | ○ | ○ | ○ |
| Example 23 | En | 3 | done | bis(2,2,6,6-tetramethyl-4-piperidyl)sebacate | absent | 60 | 200 | ○ | ○ | ○ |
| Example 24 | En | 3 | done | phenothiazine | absent | 58 | 193 | ○ | ○ | ○ |
| Example 25 | En | 3 | done | 2-mercaptobenzimidazole | absent | 53 | 176 | ○ | ○ | ○ |
| Example 26 | En | 3 | done | triphenyl phosphite | absent | 54 | 179 | ○ | ○ | ○ |
| Example 27 | En | 3 | done | dibenzyl disulfide | absent | 51 | 170 | ○ | ○ | ○ |
| Example 28 | En | 3 | done | didodecyl-3,3'-thiodipropionate | absent | 52 | 173 | ○ | ○ | ○ |
| Example 29 | En | 3 | done | DL-α-lipoic acid | absent | 50 | 167 | ○ | ○ | ○ |
| Example 30 | En | 3 | done | retinoic acid | absent | 51 | 170 | ○ | ○ | ○ |
| Example 31 | En | 4 | done | rutin | absent | 80 | 133 | ○ | ○ | ○ |
| Example 32 | En | 4 | done | 2,6-di-tert-butyl-4-hydroxymethylphenol | absent | 78 | 130 | ○ | ○ | ○ |
| Example 33 | En | 4 | done | bis(2,2,6,6-tetramethyl-4-piperidyl)sebacate | absent | 77 | 129 | ○ | ○ | ○ |
| Example 34 | En | 4 | done | phenothiazine | absent | 76 | 127 | ○ | ○ | ○ |
| Example 35 | En | 4 | done | 2-mercaptobenzimidazole | absent | 73 | 122 | ○ | ○ | ○ |
| Example 36 | En | 4 | done | triphenyl phosphite | absent | 74 | 123 | ○ | ○ | ○ |
| Example 37 | En | 4 | done | dibenzyl disulfide | absent | 72 | 120 | ○ | ○ | ○ |
| Example 38 | En | 4 | done | didodecyl-3,3'-thiodipropionate | absent | 73 | 121 | ○ | ○ | ○ |
| Example 39 | En | 4 | done | DL-α-lipoic acid | absent | 72 | 119 | ○ | ○ | ○ |
| Example 40 | En | 4 | done | retinoic acid | absent | 72 | 120 | ○ | ○ | ○ |

En: Entellan New

TABLE 3-3

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 41 | En | 5 | done | rutin | absent | 65 | 217 | ○ | ○ | ○ |
| Example 42 | En | 5 | done | 2,6-di-tert-butyl-4-hydroxymethylphenol | absent | 62 | 205 | ○ | ○ | ○ |
| Example 43 | En | 5 | done | bis(2,2,6,6-tetramethyl-4-piperidyl)sebacate | absent | 60 | 200 | ○ | ○ | ○ |

TABLE 3-3-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 44 | En | 5 | done | phenothiazine | absent | 58 | 193 | ○ | ○ | ○ |
| Example 45 | En | 5 | done | 2-mercaptobenzimidazole | absent | 53 | 176 | ○ | ○ | ○ |
| Example 46 | En | 5 | done | triphenyl phosphite | absent | 54 | 179 | ○ | ○ | ○ |
| Example 47 | En | 5 | done | dibenzyl disulfide | absent | 51 | 170 | ○ | ○ | ○ |
| Example 48 | En | 5 | done | didodecyl-3,3'-thiodipropionate | absent | 52 | 173 | ○ | ○ | ○ |
| Example 49 | En | 5 | done | DL-α-lipoic acid | absent | 50 | 167 | ○ | ○ | ○ |
| Example 50 | En | 5 | done | retinoic acid | absent | 51 | 170 | ○ | ○ | ○ |
| Example 51 | En | 6 | done | rutin | absent | 63 | 250 | ○ | ○ | ○ |
| Example 52 | En | 6 | done | 2,6-di-tert-butyl-4-hydroxymethylphenol | absent | 59 | 235 | ○ | ○ | ○ |
| Example 53 | En | 6 | done | bis(2,2,6,6-tetramethyl-4-piperidyl)sebacate | absent | 57 | 229 | ○ | ○ | ○ |
| Example 54 | En | 6 | done | phenothiazine | absent | 55 | 220 | ○ | ○ | ○ |
| Example 55 | En | 6 | done | 2-mercaptobenzimidazole | absent | 49 | 198 | ○ | ○ | ○ |
| Example 56 | En | 6 | done | triphenyl phosphite | absent | 50 | 201 | ○ | ○ | ○ |
| Example 57 | En | 6 | done | dibenzyl disulfide | absent | 48 | 190 | ○ | ○ | ○ |
| Example 58 | En | 6 | done | didodecyl-3,3'-thiodipropionate | absent | 48 | 194 | ○ | ○ | ○ |
| Example 59 | En | 6 | done | DL-α-lipoic acid | absent | 47 | 186 | ○ | ○ | ○ |
| Example 60 | En | 6 | done | retinoic acid | absent | 48 | 190 | ○ | ○ | ○ |

En: Entellan New

TABLE 3-4

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 61 | En | 7 | done | rutin | absent | 78 | 141 | ○ | ○ | ○ |
| Example 62 | En | 7 | done | 2,6-di-tert-butyl-4-hydroxymethylphenol | absent | 75 | 137 | ○ | ○ | ○ |
| Example 63 | En | 7 | done | bis(2,2,6,6-tetramethyl-4-piperidyl)sebacate | absent | 74 | 135 | ○ | ○ | ○ |
| Example 64 | En | 7 | done | phenothiazine | absent | 73 | 133 | ○ | ○ | ○ |
| Example 65 | En | 7 | done | 2-mercaptobenzimidazole | absent | 70 | 127 | ○ | ○ | ○ |
| Example 66 | En | 7 | done | triphenyl phosphite | absent | 70 | 128 | ○ | ○ | ○ |
| Example 67 | En | 7 | done | dibenzyl disulfide | absent | 69 | 125 | ○ | ○ | ○ |
| Example 68 | En | 7 | done | didodecyl-3,3'-thiodipropionate | absent | 69 | 126 | ○ | ○ | ○ |
| Example 69 | En | 7 | done | DL-α-lipoic acid | absent | 68 | 124 | ○ | ○ | ○ |
| Example 70 | En | 7 | done | retinoic acid | absent | 69 | 125 | ○ | ○ | ○ |
| Example 71 | En | 8 | done | rutin | absent | 63 | 250 | ○ | ○ | ○ |
| Example 72 | En | 8 | done | 2,6-di-tert-butyl-4-hydroxymethylphenol | absent | 59 | 235 | ○ | ○ | ○ |
| Example 73 | En | 8 | done | bis(2,2,6,6-tetramethyl-4-piperidyl)sebacate | absent | 57 | 229 | ○ | ○ | ○ |

TABLE 3-4-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 74 | En | 8 | done | phenothiazine | absent | 55 | 220 | ○ | ○ | ○ |
| Example 75 | En | 8 | done | 2-mercaptobenzimidazole | absent | 49 | 198 | ○ | ○ | ○ |
| Example 76 | En | 8 | done | triphenyl phosphite | absent | 50 | 201 | ○ | ○ | ○ |
| Example 77 | En | 8 | done | dibenzyl disulfide | absent | 48 | 190 | ○ | ○ | ○ |
| Example 78 | En | 8 | done | didodecyl-3,3'-thiodipropionate | absent | 48 | 194 | ○ | ○ | ○ |
| Example 79 | En | 8 | done | DL-α-lipoic acid | absent | 47 | 186 | ○ | ○ | ○ |
| Example 80 | En | 8 | done | retinoic acid | absent | 48 | 190 | ○ | ○ | ○ |

En: Entellan New

TABLE 3-5

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 81 | En | 9 | done | rutin | absent | 70 | 175 | ○ | ○ | ○ |
| Example 82 | En | 9 | done | 2,6-di-tert-butyl-4-hydroxymethylphenol | absent | 67 | 168 | ○ | ○ | ○ |
| Example 83 | En | 9 | done | bis(2,2,6,6-tetramethyl-4-piperidyl)sebacate | absent | 66 | 165 | ○ | ○ | ○ |
| Example 84 | En | 9 | done | phenothiazine | absent | 64 | 160 | ○ | ○ | ○ |
| Example 85 | En | 9 | done | 2-mercaptobenzimidazole | absent | 60 | 149 | ○ | ○ | ○ |
| Example 86 | En | 9 | done | triphenyl phosphite | absent | 60 | 151 | ○ | ○ | ○ |
| Example 87 | En | 9 | done | dibenzyl disulfide | absent | 58 | 145 | ○ | ○ | ○ |
| Example 88 | En | 9 | done | didodecyl-3,3'-thiodipropionate | absent | 59 | 147 | ○ | ○ | ○ |
| Example 89 | En | 9 | done | DL-α-lipoic acid | absent | 57 | 143 | ○ | ○ | ○ |
| Example 90 | En | 9 | done | retinoic acid | absent | 58 | 145 | ○ | ○ | ○ |
| Example 91 | En | 10 | done | rutin | absent | 85 | 121 | ○ | ○ | ○ |
| Example 92 | En | 10 | done | 2,6-di-tert-butyl-4-hydroxymethylphenol | absent | 84 | 119 | ○ | ○ | ○ |
| Example 93 | En | 10 | done | bis(2,2,6,6-tetramethyl-4-piperidyl)sebacate | absent | 83 | 118 | ○ | ○ | ○ |
| Example 94 | En | 10 | done | phenothiazine | absent | 82 | 117 | ○ | ○ | ○ |
| Example 95 | En | 10 | done | 2-mercaptobenzimidazole | absent | 80 | 114 | ○ | ○ | ○ |
| Example 96 | En | 10 | done | triphenyl phosphite | absent | 80 | 114 | ○ | ○ | ○ |
| Example 97 | En | 10 | done | dibenzyl disulfide | absent | 79 | 113 | ○ | ○ | ○ |
| Example 98 | En | 10 | done | didodecyl-3,3'-thiodipropionate | absent | 79 | 113 | ○ | ○ | ○ |
| Example 99 | En | 10 | done | DL-α-lipoic acid | absent | 79 | 112 | ○ | ○ | ○ |
| Example 100 | En | 10 | done | retinoic acid | absent | 79 | 113 | ○ | ○ | ○ |

En: Entellan New

TABLE 3-6

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 101 | En | 11 | done | rutin | absent | 70 | 175 | ○ | ○ | ○ |
| Example 102 | En | 11 | done | 2,6-di-tert-butyl-4-hydroxymethylphenol | absent | 67 | 168 | ○ | ○ | ○ |
| Example 103 | En | 11 | done | bis(2,2,6,6-tetramethyl-4-piperidyl)sebacate | absent | 66 | 165 | ○ | ○ | ○ |
| Example 104 | En | 11 | done | phenothiazine | absent | 64 | 160 | ○ | ○ | ○ |
| Example 105 | En | 11 | done | 2-mercaptobenzimidazole | absent | 60 | 149 | ○ | ○ | ○ |
| Example 106 | En | 11 | done | triphenyl phosphite | absent | 60 | 151 | ○ | ○ | ○ |
| Example 107 | En | 11 | done | dibenzyl disulfide | absent | 58 | 145 | ○ | ○ | ○ |
| Example 108 | En | 11 | done | didodecyl-3,3'-thiodipropionate | absent | 59 | 147 | ○ | ○ | ○ |
| Example 109 | En | 11 | done | DL-α-lipoic acid | absent | 57 | 143 | ○ | ○ | ○ |
| Example 110 | En | 11 | done | retinoic acid | absent | 58 | 145 | ○ | ○ | ○ |
| Example 111 | En | 12 | done | rutin | absent | 88 | 117 | ○ | ○ | ○ |
| Example 112 | En | 12 | done | 2,6-di-tert-butyl-4-hydroxymethylphenol | absent | 86 | 115 | ○ | ○ | ○ |
| Example 113 | En | 12 | done | bis(2,2,6,6-tetramethyl-4-piperidyl)sebacate | absent | 86 | 114 | ○ | ○ | ○ |
| Example 114 | En | 12 | done | phenothiazine | absent | 85 | 113 | ○ | ○ | ○ |
| Example 115 | En | 12 | done | 2-mercaptobenzimidazole | absent | 83 | 111 | ○ | ○ | ○ |
| Example 116 | En | 12 | done | triphenyl phosphite | absent | 83 | 111 | ○ | ○ | ○ |
| Example 117 | En | 12 | done | dibenzyl disulfide | absent | 83 | 110 | ○ | ○ | ○ |
| Example 118 | En | 12 | done | didodecyl-3,3'-thiodipropionate | absent | 83 | 110 | ○ | ○ | ○ |
| Example 119 | En | 12 | done | DL-α-lipoic acid | absent | 82 | 110 | ○ | ○ | ○ |
| Example 120 | En | 12 | done | retinoic acid | absent | 90 | 105 | ○ | ○ | ○ |

En: Entellan New

TABLE 3-7

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 121 | En | 13 | done | rutin | absent | 93 | 109 | ○ | ○ | ○ |
| Example 122 | En | 13 | done | 2,6-di-tert-butyl-4-hydroxymethylphenol | absent | 92 | 108 | ○ | ○ | ○ |
| Example 123 | En | 13 | done | bis(2,2,6,6-tetramethyl-4-piperidyl)sebacate | absent | 91 | 108 | ○ | ○ | ○ |
| Example 124 | En | 13 | done | phenothiazine | absent | 91 | 107 | ○ | ○ | ○ |
| Example 125 | En | 13 | done | 2-mercaptobenzimidazole | absent | 90 | 106 | ○ | ○ | ○ |
| Example 126 | En | 13 | done | triphenyl phosphite | absent | 90 | 106 | ○ | ○ | ○ |
| Example 127 | En | 13 | done | dibenzyl disulfide | absent | 90 | 105 | ○ | ○ | ○ |
| Example 128 | En | 13 | done | didodecyl-3,3'-thiodipropionate | absent | 90 | 106 | ○ | ○ | ○ |
| Example 129 | En | 13 | done | DL-α-lipoic acid | absent | 89 | 105 | ○ | ○ | ○ |
| Example 130 | En | 13 | done | retinoic acid | absent | 90 | 105 | ○ | ○ | ○ |

TABLE 3-7-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 131 | Pm | 3 | done | rutin | absent | 65 | 217 | ○ | ○ | ○ |
| Example 132 | Pm | 3 | done | 2,6-di-tert-butyl-4-hydroxymethylphenol | absent | 62 | 205 | ○ | ○ | ○ |
| Example 133 | Pm | 3 | done | bis(2,2,6,6-tetramethyl-4-piperidyl)sebacate | absent | 60 | 200 | ○ | ○ | ○ |
| Example 134 | Pm | 3 | done | phenothiazine | absent | 58 | 193 | ○ | ○ | ○ |
| Example 135 | Pm | 3 | done | 2-mercaptobenzimidazole | absent | 53 | 176 | ○ | ○ | ○ |
| Example 136 | Pm | 3 | done | triphenyl phosphite | absent | 54 | 179 | ○ | ○ | ○ |
| Example 137 | Pm | 3 | done | dibenzyl disulfide | absent | 51 | 170 | ○ | ○ | ○ |
| Example 138 | Pm | 3 | done | didodecyl-3,3'-thiodipropionate | absent | 52 | 173 | ○ | ○ | ○ |
| Example 139 | Pm | 3 | done | DL-α-lipoic acid | absent | 50 | 167 | ○ | ○ | ○ |
| Example 140 | Pm | 3 | done | retinoic acid | absent | 51 | 170 | ○ | ○ | ○ |

TABLE 4

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 141 | En | 1 | done | none | absent | 15 | — | ○ | ○ | ○ |
| Example 142 | En | 2 | done | none | absent | 30 | — | ○ | ○ | ○ |
| Example 143 | En | 3 | done | none | absent | 30 | — | ○ | ○ | ○ |
| Example 144 | En | 4 | done | none | absent | 60 | — | ○ | ○ | ○ |
| Example 145 | En | 5 | done | none | absent | 30 | — | ○ | ○ | ○ |
| Example 146 | En | 6 | done | none | absent | 25 | — | ○ | ○ | ○ |
| Example 147 | En | 7 | done | none | absent | 55 | — | ○ | ○ | ○ |
| Example 148 | En | 8 | done | none | absent | 25 | — | ○ | ○ | ○ |
| Example 149 | En | 9 | done | none | absent | 40 | — | ○ | ○ | ○ |
| Example 150 | En | 10 | done | none | absent | 70 | — | ○ | ○ | ○ |
| Example 151 | En | 11 | done | none | absent | 40 | — | ○ | ○ | ○ |
| Example 152 | En | 12 | done | none | absent | 75 | — | ○ | ○ | ○ |
| Example 153 | En | 13 | done | none | absent | 85 | — | ○ | ○ | ○ |
| Example 154 | Pm | 3 | done | none | absent | 30 | — | ○ | ○ | ○ |

En: Entellan New,
Pm: PARA Mount-N

TABLE 5-1

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 155 | En | 1 | done | cyanidin | absent | 58 | 383 | ○ | ○ | x |
| Example 156 | En | 1 | done | p-phenylazophenol | absent | 49 | 327 | ○ | ○ | x |
| Example 157 | En | 1 | done | 4-nitroaniline | absent | 47 | 315 | ○ | ○ | x |
| Example 158 | En | 1 | done | lycopene | absent | 42 | 281 | ○ | ○ | x |
| Example 159 | En | 2 | done | cyanidin | absent | 65 | 217 | ○ | ○ | x |
| Example 160 | En | 2 | done | p-phenylazophenol | absent | 58 | 193 | ○ | ○ | x |
| Example 161 | En | 2 | done | 4-nitroaniline | absent | 57 | 189 | ○ | ○ | x |
| Example 162 | En | 2 | done | lycopene | absent | 52 | 175 | ○ | ○ | x |

TABLE 5-1-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 163 | En | 3 | done | cyanidin | absent | 65 | 217 | ○ | ○ | x |
| Example 164 | En | 3 | done | p-phenylazophenol | absent | 58 | 193 | ○ | ○ | x |
| Example 165 | En | 3 | done | 4-nitroaniline | absent | 57 | 189 | ○ | ○ | x |
| Example 166 | En | 3 | done | lycopene | absent | 52 | 175 | ○ | ○ | x |
| Example 167 | En | 4 | done | cyanidin | absent | 80 | 133 | ○ | ○ | x |
| Example 168 | En | 4 | done | p-phenylazophenol | absent | 76 | 127 | ○ | ○ | x |
| Example 169 | En | 4 | done | 4-nitroaniline | absent | 75 | 125 | ○ | ○ | x |
| Example 170 | En | 4 | done | lycopene | absent | 73 | 121 | ○ | ○ | x |
| Example 171 | En | 5 | done | cyanidin | absent | 65 | 217 | ○ | ○ | x |
| Example 172 | En | 5 | done | p-phenylazophenol | absent | 58 | 193 | ○ | ○ | x |
| Example 173 | En | 5 | done | 4-nitroaniline | absent | 57 | 189 | ○ | ○ | x |
| Example 174 | En | 5 | done | lycopene | absent | 52 | 175 | ○ | ○ | x |

En: Entellan New

TABLE 5-2

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 175 | En | 6 | done | cyanidin | absent | 63 | 250 | ○ | ○ | x |
| Example 176 | En | 6 | done | p-phenylazophenol | absent | 55 | 220 | ○ | ○ | x |
| Example 177 | En | 6 | done | 4-nitroaniline | absent | 54 | 214 | ○ | ○ | x |
| Example 178 | En | 6 | done | lycopene | absent | 49 | 196 | ○ | ○ | x |
| Example 179 | En | 7 | done | cyanidin | absent | 78 | 141 | ○ | ○ | x |
| Example 180 | En | 7 | done | p-phenylazophenol | absent | 73 | 133 | ○ | ○ | x |
| Example 181 | En | 7 | done | 4-nitroaniline | absent | 72 | 131 | ○ | ○ | x |
| Example 182 | En | 7 | done | lycopene | absent | 69 | 126 | ○ | ○ | x |
| Example 183 | En | 8 | done | cyanidin | absent | 63 | 250 | ○ | ○ | x |
| Example 184 | En | 8 | done | p-phenylazophenol | absent | 55 | 220 | ○ | ○ | x |
| Example 185 | En | 8 | done | 4-nitroaniline | absent | 54 | 214 | ○ | ○ | x |
| Example 186 | En | 8 | done | lycopene | absent | 49 | 196 | ○ | ○ | x |
| Example 187 | En | 9 | done | cyanidin | absent | 70 | 175 | ○ | ○ | x |
| Example 188 | En | 9 | done | p-phenylazophenol | absent | 64 | 160 | ○ | ○ | x |
| Example 189 | En | 9 | done | 4-nitroaniline | absent | 63 | 157 | ○ | ○ | x |
| Example 190 | En | 9 | done | lycopene | absent | 59 | 148 | ○ | ○ | x |
| Example 191 | En | 10 | done | cyanidin | absent | 85 | 121 | ○ | ○ | x |
| Example 192 | En | 10 | done | p-phenylazophenol | absent | 82 | 117 | ○ | ○ | x |

TABLE 5-2-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 193 | En | 10 | done | 4-nitroaniline | absent | 81 | 116 | ○ | ○ | x |
| Example 194 | En | 10 | done | lycopene | absent | 80 | 114 | ○ | ○ | x |

En: Entellan New

TABLE 5-3

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Example 195 | En | 11 | done | cyanidin | absent | 70 | 175 | ○ | ○ | x |
| Example 196 | En | 11 | done | p-phenylazophenol | absent | 64 | 160 | ○ | ○ | x |
| Example 197 | En | 11 | done | 4-nitroaniline | absent | 63 | 157 | ○ | ○ | x |
| Example 198 | En | 11 | done | lycopene | absent | 59 | 148 | ○ | ○ | x |
| Example 199 | En | 12 | done | cyanidin | absent | 88 | 117 | ○ | ○ | x |
| Example 200 | En | 12 | done | p-phenylazophenol | absent | 85 | 113 | ○ | ○ | x |
| Example 201 | En | 12 | done | 4-nitroaniline | absent | 85 | 113 | ○ | ○ | x |
| Example 202 | En | 12 | done | lycopene | absent | 90 | 106 | ○ | ○ | x |
| Example 203 | En | 13 | done | cyanidin | absent | 93 | 109 | ○ | ○ | x |
| Example 204 | En | 13 | done | p-phenylazophenol | absent | 91 | 107 | ○ | ○ | x |
| Example 205 | En | 13 | done | 4-nitroaniline | absent | 91 | 107 | ○ | ○ | x |
| Example 206 | En | 13 | done | lycopene | absent | 90 | 106 | ○ | ○ | x |

En: Entellan New

TABLE 6

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Comparative Example 1 | Fm | 3 | done | absent | absent | 15 | — | ○ | x | x |
| Comparative Example 2 | En | 1 | absent | absent | absent | n.d. | — | x | ○ | ○ |
| Comparative Example 3 | En | 2 | absent | absent | absent | n.d. | — | x | ○ | ○ |
| Comparative Example 4 | En | 3 | absent | absent | absent | n.d. | — | x | ○ | ○ |
| Comparative Example 5 | En | 4 | absent | absent | absent | n.d. | — | x | ○ | ○ |
| Comparative Example 6 | En | 5 | absent | absent | absent | n.d. | — | x | ○ | ○ |
| Comparative Example 7 | En | 6 | absent | absent | absent | n.d. | — | x | ○ | ○ |
| Comparative Example 8 | En | 7 | absent | absent | absent | n.d. | — | x | ○ | ○ |
| Comparative Example 9 | En | 8 | absent | absent | absent | n.d. | — | x | ○ | ○ |
| Comparative Example 10 | En | 9 | absent | absent | absent | n.d. | — | x | ○ | ○ |
| Comparative Example 11 | En | 10 | absent | absent | absent | n.d. | — | x | ○ | ○ |

TABLE 6-continued

| | Mounting medium | Fluorescent label | Immobilization treatment | Discoloration inhibitor | Absorption by discoloration inhibitor | Brightness retention rate [%] | Improvement rate [%] | Maintenance of fluorescent staining properties | Storage property | Transparency |
|---|---|---|---|---|---|---|---|---|---|---|
| Comparative Example 12 | En | 11 | absent | absent | absent | n.d. | — | x | ○ | ○ |
| Comparative Example 13 | En | 12 | absent | absent | absent | n.d. | — | x | ○ | ○ |
| Comparative Example 14 | En | 13 | absent | absent | absent | n.d. | — | x | ○ | ○ |
| Comparative Example 15 | Pm | 3 | absent | absent | absent | n.d. | — | x | ○ | ○ |

En: Entellan New,
Pm: PARA Mount-N,
Fm: Fluoromount
n.d.: not determined

As a result of these evaluations, it was shown that, even when a mounting medium comprising a solvent not freely miscible with water (oil-based mounting medium) is used, by performing an immobilization treatment, a fluorescently stained specimen which has no reduction in the fluorescent staining properties (reduction of the light-emitting parts) and no bleeding of stains and may thus be actually used for observation can be prepared. In addition, it was shown that an addition of a discoloration inhibitor improves the brightness retention rate. Furthermore, it was also shown that, by using a discoloration inhibitor showing no absorption, a transparent section slide that is more suitable for fluorescence observation can be obtained.

The invention claimed is:

1. A biological substance detection method for specifically detecting a biological substance from a pathological specimen, said method comprising the steps, in the following order, of:
   activating said biological substance of said specimen;
   blocking said specimen;
   immunostaining said specimen with a fluorescent label;
   immobilizing the immunostained specimen with an immobilization solution selected from the group consisting of formalin, paraformaldehyde, and glutaraldehyde;
   morphological staining the immobilized specimen with a staining agent for morphological observation; and
   mounting the morphological-stained specimen using an oil-based mounting medium comprising a resin, an organic solvent not freely miscible with water, and a discoloration inhibitor which is soluble in said organic solvent and which is selected from the group consisting of phenols derived from natural products and hindered phenols,
   wherein the phenols derived from the natural products are rutin, catechin, or quercetin,
   the hindered phenols are 2,6-di-tert-butyl-4-hydroxymethylphenol, 1,3,5-trimethyl-2,4,6-tris(3,5-di-t-butyl-4-hydroxybenzyl)benzene, 3,5-di-t-butyl-4-hydroxybenzyl phosphonate diethyl ester, and
   a section slide prepared using said oil-based mounting medium comprising said discoloration inhibitor is transparent.

2. The biological substance detection method according to claim 1, wherein said fluorescent label comprises at least one selected from the group consisting of fluorescent dye-containing nanoparticles and fluorescent nanoparticle-containing particles.

3. The biological substance detection method according to claim 1, wherein said organic solvent not freely miscible with water comprises at least one selected from the group consisting aromatic hydrocarbons, unsaturated hydrocarbons, ketones, esters, ethers and alcohols.

4. The biological substance detection method according to claim 1, wherein said organic solvent not freely miscible with water comprises at least one selected from the group consisting of xylene, toluene and limonene.

5. The biological substance detection method according to claim 1, wherein said discoloration inhibitor does not absorb light in an absorption wavelength range of 450 to 600 nm.

6. A biological substance detection kit used for the biological substance detection method according to claim 1, said kit comprising:
   an oil-based mounting medium, a discoloration inhibitor, a fluorescent label for immunostaining, and a fluorescent labeling reagent; and
   an instruction manual that describes said biological substance detection method,
   wherein the oil-based mounting medium comprises a resin, an organic solvent not freely miscible with water, and the discoloration inhibitor which is soluble in the organic solvent and which is selected from the group consisting of phenols derived from natural products and hindered phenols,
   the phenols derived from the natural products are rutin, catechin, or quercetin, and
   the hindered phenols are 2,6-di-tert-butyl-4-hydroxymethylphenol, 1,3,5-trimethyl-2,4,6-tris(3,5-di-t-butyl-4-hydroxybenzyl)benzene, or 3,5-di-t-butyl-4-hydroxybenzyl phosphonate diethyl ester.

7. A pathological specimen used for the biological substance detection method according to claim 1,
   wherein said pathological specimen was subjected to the steps, in the following order:
   the activating step the biological substance of the specimen;
   the blocking step of the specimen;
   the immunostaining step using the fluorescent label for specifically detecting the biological substance;
   the immobilization step using the immobilization solution selected from the group consisting of formalin, paraformaldehyde, and glutaraldehyde;
   the morphological staining step using the staining agent for morphological observation; and
   the mounting step using the oil-based mounting medium comprising the resin, the organic solvent not freely miscible with water, and the discoloration inhibitor which is soluble in said organic solvent and which is selected from the group consisting of the phenols derived from natural products and the hindered phenols, and wherein the pathological specimen comprises:
the oil-based mounting medium comprising the resin, the organic solvent, and the discoloration inhibitor;
the pathological specimen mounted on the medium;
the fluorescent label bound and immobilized to the biological substance; and
the staining agent contacting with the pathological specimen, and
the phenols derived from the natural products are rutin, catechin, or quercetin,
the hindered phenols are 2,6-di-tert-butyl-4-hydroxymethylphenol, 1,3,5-trimethyl-2,4,6-tris(3,5-di-t-butyl-4-hydroxybenzyl)benzene, or 3,5-di-t-butyl-4-hydroxybenzyl phosphonate diethyl ester.

8. The biological substance detection method according to claim 1, wherein the method further comprises, after the step of mounting the morphological-stained specimen, the steps of:
observing an image produced by the immunostaining by irradiating the pathological specimen with an excitation light having a wavelength appropriate for the fluorescent label to emit fluorescence; and
observing an image produced by the morphological staining under the same observation conditions as those of a light microscope.

9. The biological substance detection method according to claim 1, wherein the pathological specimen is a pathological tissue specimen.

* * * * *